(12) United States Patent
Devane et al.

(10) Patent No.: US 7,928,092 B2
(45) Date of Patent: Apr. 19, 2011

(54) FORMULATIONS AND METHODS OF TREATING INFLAMMATORY BOWEL DISEASE

(75) Inventors: John Devane, Athlone (IE); Jackie Butler, Athlone (IE)

(73) Assignee: AGI Therapeutics Ltd., Athlone (IE)

( * ) Notice: Subject to any disclaimer, the term of this patent is extended or adjusted under 35 U.S.C. 154(b) by 0 days.

(21) Appl. No.: 12/797,655

(22) Filed: Jun. 10, 2010

(65) Prior Publication Data

US 2010/0278917 A1 Nov. 4, 2010

Related U.S. Application Data

(63) Continuation of application No. 10/930,743, filed on Sep. 1, 2004, now Pat. No. 7,737,133.

(60) Provisional application No. 60/499,365, filed on Sep. 3, 2003.

(51) Int. Cl.
| | |
|---|---|
| A61K 31/60 | (2006.01) |
| A61K 31/603 | (2006.01) |
| A61K 31/606 | (2006.01) |
| A61K 31/609 | (2006.01) |
| A61K 31/612 | (2006.01) |
| A61K 31/616 | (2006.01) |
| A61K 31/618 | (2006.01) |
| A61K 31/625 | (2006.01) |

(52) U.S. Cl. ........ 514/159; 514/150; 514/160; 514/161; 514/162; 514/163; 514/164; 514/165; 514/166

(58) Field of Classification Search .................. 514/150, 514/159, 160, 161, 162, 163, 164, 165, 166
See application file for complete search history.

(56) References Cited

U.S. PATENT DOCUMENTS

| | | |
|---|---|---|
| 4,374,932 A | 2/1983 | Pitzele et al. |
| 4,496,553 A | 1/1985 | Halskov |
| 4,559,330 A | 12/1985 | Agback et al. |
| 4,591,584 A | 5/1986 | Agback |
| 4,608,048 A | 8/1986 | Cortese et al. |
| 4,627,851 A | 12/1986 | Wong et al. |
| 4,693,895 A | 9/1987 | Wong et al. |
| 4,705,515 A | 11/1987 | Wong et al. |
| 4,880,794 A | 11/1989 | Halskov |
| 4,904,474 A | 2/1990 | Theeuwes et al. |
| 4,980,173 A | 12/1990 | Halskov |
| 5,041,431 A | 8/1991 | Halskov |
| 5,482,718 A | 1/1996 | Shah et al. |
| 5,505,966 A | 4/1996 | Edman et al. |
| 5,519,014 A | 5/1996 | Borody |
| 5,541,170 A | 7/1996 | Rhodes et al. |
| 5,541,171 A | 7/1996 | Rhodes et al. |
| 5,681,584 A | 10/1997 | Savastano et al. |
| 5,716,648 A | 2/1998 | Halskov et al. |
| 5,840,332 A | 11/1998 | Lerner et al. |
| 5,866,619 A | 2/1999 | Sintov et al. |
| 6,004,581 A | 12/1999 | Jepsen et al. |
| 6,277,412 B1 | 8/2001 | Otterbeck |
| 6,506,407 B2 | 1/2003 | Watanabe et al. |
| 6,551,620 B2 | 4/2003 | Otterbeck |
| 6,602,915 B2 | 8/2003 | Uhrich |
| 6,733,789 B1 | 5/2004 | Stark et al. |
| 6,897,205 B2 | 5/2005 | Beckert et al. |
| 6,962,717 B1 | 11/2005 | Huber et al. |
| 7,737,133 B2 * | 6/2010 | Devane et al. ................ 514/159 |
| 2001/0026807 A1 | 10/2001 | Watts |
| 2001/0036473 A1 | 11/2001 | Scott et al. |
| 2002/0098235 A1 | 7/2002 | Dittmar et al. |
| 2002/0192282 A1 | 12/2002 | Beckert et al. |
| 2005/0090473 A1 | 4/2005 | Devane et al. |
| 2006/0223787 A1 * | 10/2006 | Devane et al. ................ 514/159 |

FOREIGN PATENT DOCUMENTS

| | | |
|---|---|---|
| EP | 0 140 848 A1 | 5/1985 |
| EP | 0 453 001 A1 | 10/1991 |
| EP | 1 101 490 A1 | 5/2001 |
| FR | 2 692 484 A1 | 12/1993 |
| WO | WO 95/16451 | 6/1995 |
| WO | WO 00/76481 A1 | 12/2000 |
| WO | WO 02/17887 A1 | 3/2002 |

OTHER PUBLICATIONS

"Asacol® (mesalamine) Delayed-Release Tablets," Asacol (mesalamine), pp. 1-8, 2000.
"Azulfidine® sulfasalazine tablets, USP," pp. 1-18, 2002.
Ardizzone, S. et al., "Is Maintenance Therapy Always Necessary for Patients With Ulcerative Colitis in Remission?," *Aliment Pharm. Ther.*, vol. 13, No. 3, pp. 373-379, (1999).
Basit et al., "Perspectives on Colonic Drug Delivery," *Business Briefing: Pharmatech*, pp. 185-190 (2003).
Bondesen, S. et al., "5- Aminosalicylic Acid in Patients with an Ileo-Rectal Anastomosis A Comparison of the Fate of Sulfasalazine and Pentasa," *Eur. J. Clin . Pharmacol.*, vol. 31, pp. 23-26, (1986).
Bondesen, S. et al., "Steady-State Kinetics of 5-Aminosalicylic Acid and Sulfapyridine During Sulfasalazine Prophylaxis in Ulcerative Colitis," *Scan. J. Gastroentero.*, vol. 21, No. 6, pp. 693-700, (1986).
Bondesen, S. et al., "Pharmacokinetics of 5-Aminosalicylic Acid in Man Following Administration of Intravenous Bolus and Per Os Slow-Release Formulation," *Digest. Dis. Sci.*, vol. 36, No. 12, pp. 1735-1740, (1991).
Bresci, G. et al., "Long-Term Therapy With 5-Aminosalicylic Acid in Crohn's Disease: is it Useful? Our Four Years Experience," *Int. J. Clin. Pharm. Res.*, vol. XIV, No. 4, pp. 133-138, (1994).

(Continued)

*Primary Examiner* — Jason M Nolan
(74) *Attorney, Agent, or Firm* — Finnegan, Henderson, Farabow, Garrett & Dunner, LLP

(57) ABSTRACT

Methods and formulations for treating inflammatory bowel disease are disclosed. The methods and formulations include, but are not limited to, methods and formulations for delivering effective concentrations of 4-aminosalicylic acid and/or 5-aminosalicylic acid to affected areas of the intestine. The methods and formulations comprise modified-release elements, providing for drug delivery to the affected or desired area. Diseases and conditions treatable with the present invention include Crohn's disease and ulcerative colitis.

9 Claims, No Drawings

OTHER PUBLICATIONS

Brignola, C. et al., "Placebo-Controlled Trial of Oral 5-ASA in Relapse Prevention of Crohn's Disease," *Digest. Dis. Sci.*, vol. 37, No. 1, pp. 29-32, (1992).

Brunner, M. et al., "Gastrointestinal Transit and 5-ASA Release From A New Mesalazine Extended-Release Formulation," *Aliment Pharm. Ther.*, vol. 17, pp. 395-402, (2003).

Brunner, M. et al., "Gastrointestinal Transit and Release of 5-Aminosalicylic Acid From [153]Sm-Labelled Mesalazine Pellets vs. Tablets in Male Healthy Volunteers," *Aliment Pharm. Ther.*, vol. 17 pp. 1163-1169, (2003).

Campieri, M. et al., "Oral Beclometasone Dipropionate in the Treatment of Extensive and Left-Sided Active Ulcerative Colitis: A Multicentre Randomised Study," *Aliment Pharm. Ther.*, vol. 17, pp. 1471-1480 (2003).

Chourasia, M.K. et al., "Pharmaceutical Approaches to Colon Targeted Drug Delivery Systems," *J. Pharm. Pharmaceut Sci.*, vol. 6(1) pp. 33-66, (2003).

Christensen, L. A. et al., "5-Aminosalicylic Acid Derivatives. Clinical and Pharmaceutical Evaluation," *Neth J. Med.*, vol. 35, Suppl. 1:S3:10, (1989).

Christensen, L. A. et al., "Topical and Systemic Availability of 5-Aminosalicylate: Comparisons of Three Controlled Release Preparations in Man," *Aliment Pharm. Ther.*, vol. 4, pp. 523-533, (1990).

Christensen, L. et al., "Bioavailability of 5-Aminosalicylic Acid from Slow Release 5-Aminosalicylic Acid Drug and Sulfasalazine in Normal Children," *Digest. Dis. Sci.*, vol. 38, No. 10, pp. 1831-1836, (1993).

Christensen, L. A. et al., "Comparative Biovailability of 5-Aminosalicyclic Acid From a Controlled Release Preparation and an Azo-bond Preparation," *Aliment Pharm. Ther.*, vol. 8, pp. 289-294, (1994).

Christensen, L. et al., "5-Aminosalicylic Acid Containing Drugs Delivery, Fate, and Possible Clinical Implications in Man," *Dan. Med. Bull.*, vol. 47, No. 1, pp. 20-41, (2000).

Clemett, D. et al., "Prolonged-Release Mesalazine A Review of Its Therapeutic Potential in Ulcerative Colitis and Crohn's Disease," *Drugs*, vol. 59 No. 4, pp. 929-956, (2000).

Corey, A. E. et al., "Biovailabily of single and Multiple Dose of Enteric-Coated Mesalamine and Sulphasalazine," *J. Int. Med. Res.*, vol. 18, pp. 441-453, (1990).

Davaran, S. et al., "Synthesis and Characterization of Methacrylic Derivatives of 5-Amino Salicylic Acid with pH-Sensitive Swelling Properties," *AAPS PharmaSciTech*, vol. 2 (4) article 29 (2001).

Devane, J. et al., "Distal Ileum and Colon: Targeted Sites for 5-ASA Release," *Eur. J. Drug Metab. Phamacokinet, Spec.*, No. 3, pp. 300-303, (1991).

Dijkstra, G. et al., "Blockade of NF-κB Activation and Donation of Nitric Oxide: New Treatment Options in Inflammatory Bowel Disease?," *Scan. J. Gastroentero.*, Suppl. 236 (2002).

"Dipentum® olsalazine sodium capsules," pp. 1-17, 2001.

Ewe, K. et al., "Inflammation Does Not Decrease Intraluminal pH in Chronic Inflammatory Bowel Disease," *Digest. Dis. Sci.*, vol. 44, No. 7, pp. 1434-1439, (1999).

Fallingborg, J. et al., "Effect of Olsalazine and Mesalazine on Intraluminal pH of the Duodenum and Proximal Jerjunum in Healthy Humans," *Scan. J. Gastroentero.*, vol. 29, No. 6, pp. 498-500, (1994).

Farup, P. et al., "Mesalazine 4 g Daily Given as Prolonged-Release Granules Twice Daily and Four Times Daily Is at Least as Effective as Prolonged-Release Tablets Four Times Daily in Patients with Ulcerative Colitis," *Inflamm. Bowel Dis.*, vol. 7, No. 3, pp. 237-242, (2001).

Fernandez-Banares et al., "Collagenous and Lymphocytic Colitis: Evaluation of Clinical and Histological Features, Response to Treatment, and Long-Term Follow-Up," *Am. J. Gastroenterol.*, vol. 98, No. 2, pp. 395-402, (2003).

Fischer, C. et al. "Disposition of 5-Aminosalicylic Acid, the Active Metabolite of Sulphasalazine, in Man," *Eur. J. Clin. Pharamcol.*, vol. 25, pp. 511-515, (1983).

Florent, C. et al., "Placebo-Controlled Clinical Trial of Mesalazine in the Prevention of Early Endoscopic Recurrences After Recurrences After Resection for Crohn's Disease," *Eur J. Gastroen. Hepat.*, vol. 8, No. 3, pp. 229-233, (1996).

Fockens, P. et al., "Comparison of the Efficacy and Safety of 1.5 Compared with 3.0 g oral Slow-Release Mesalazine (Pentasa) in the Maintenance Treatment of Ulcerative Colitis," *Eur. J. Gastroen. Hepat.*, vol. 7, No. 11, pp. 1025-1030, (1995).

Forbes, A. et al., "Review Article: Oral, Modified-Release Mesalazine Formulations-Proprietary Versus Generic," *Aliment Pharm. Ther.*, vol. 17, pp. 1207-1214 (2003).

French, D. et al., "Controlled Release of Substituted Benzoic and Naphthoic Acids Using Carbopol® Gels: Measurement of Drug Concentration Profiles and Correlation to Release Rate Kinetics," *Pharmaceut. Res.*, vol. 12, No. 10, pp. 1513-1520, (1995).

Gardner, G. et al., "Disease-Modifying Antirheumatic Drugs, Potential Effects in Older Patients," *Drugs & Aging*, vol. 7, No. 6, pp. 420-437 (1995).

Gendre, J. P. et al., "Oral Mesalamine (Pentass) as Maintenanle Treatment in Crohn's Disease A Multicenter Placebo-Controlled Study" *Ann. Gastroen. Hepat.* (Paris), vol. 29, No. 5, pp. 251-256 (1993). Abstract.

Gendre, J. P. et al., "Oral Mesalamine (Pentasa) as Maintenance Treatment in Crohn's Disease: A Multicenter Placebo-Controlled Study," *Gastroenterology*, vol. 104, pp. 435-439, (1993).

Gionchetti, P. et al., "Bioavailablity of Single and Multiple Doses of a New Oral Formulation of 5-ASA in Patients With Inflammatory Bowel Disease and Healthy Volunteers," *Aliment Pharm. Ther.*, vol. 8, pp. 535-540 (1994).

Gionchetti, P. et al., "Systemic Availability of 5- Aminosaliclylic Acid: Comparison of Delayed Release and an Azo-Bond Preparation," *Aliment Pharm. Ther.*, vol. 10, No. 4, pp. 601-605, (1996).

Green, J. et al., "Nicotine: Therapeutic Potential for the Treatment of Ulcerative Colitis," *Expert Opinion on Investigational Drugs*, vol. 6, No. 1, pp. 17-21, (1997).

Griffiths, A. et al., "Slow-Release 5-Aminosalicylic Acid Therapy in Children with Small Intestinal Crohn's Disease," *J. Ped. Gastroenterol. Nutr.*, vol. 17, pp. 186-192, (1993).

Gupta, V. et al., "A Novel pH- and Time-based Multi-Unit Potential Colonic Drug Delivery System. I. Development," *Int. J. Pharmaceutics*, vol. 213, pp. 83-91, (2001).

Hall, J. et al., "Effect of Controlled Local Acetylsalicylic Acid Release on In-Vitro Platelet Adhesion to Vascular Grafts," *J. Biomaterials Appl.*, vol. 8, No. 4, pp. 361-384, (1994).

Hanauer, S. et al., "Mesalamine Capsules for Treatment of Active Ulcerative Colitis: Results of controlled Trial," *Am. J. Gastroenterol.*, vol. 88, No. 8, pp. 1188-1197, (1993).

Hanauer, S. et al., Long-Term Management of Crohn's Disease with Mesalamine Capsules (Pentasa®), *Am. J. Gastroenterol.*, vol. 88, No. 9, pp. 1343-1351, (1993).

Hardy, J. G. et al., "Localization of Drug Release Sites from an Oral Sustained-Release Formulation of 5-ASA (Pentasa®) in the Gastrointestinal Tract Using Gamma Scintigraphy," *J. Clin. Pharmacol.*, vol. 33, pp. 712-718 (1993).

Hawthorne, A. B. et al., "Immunosuppressive Drugs in Inflammatory Bowel Disease, A Review of Their Mechanisms of Efficacy and Place in Therapy," *Drugs*, vol. 38, No. 2, pp. 267-288, (1989).

Healey, J. N. C. "Gastrointestinal Transit and Release of Mesalazine Tablets in Patients with Inflammatory Bowel Disease," *Scan. J. Gastroentero.*, vol. 25, Suppl. 172, 1990.

Hu, Z. et al., "Technology to Obtain Sustained Release Characteristics of Drugs After Delivered to the Colon," *J. Drug Targeting*, vol. 6, No. 6, pp. 439-448 (1999).

International Search Report for PCT/IB2004/003059, mailed May 26, 2005.

Jhala, et al., Studies on Toxicity and Tuberculostatic Behaviour of 4:4-Biazosalicylic Acid, *Ind. J. Pharm.*, vol. 13, 3-5 (1951), pp. 3-5.

Karamanolis, D. et al., "Systemic Absorption of 5-Aminosalicylic Acid in Patients With Inactive Ulcerative Colitis Treated with Olasalazine and Mesalazine," *Eur. J. Gastroen. Hepat.*, vol. 8, No. 11, pp. 1083-1088, (1996).

Keller, J. et al., "Significance of Galenic Preparations for Luminal Release of 5-Aminosalicylic Acid in Human Small Intestinal Lumen," *Med. Klin*, vol. 93, No. 5, pp. 294-299, (1998).

Khan, et al., A pH-Dependent Colon-Targeted Oral Drug Delivery System Using Methacrylic Acid Copolymers. II. Manipulation of Drug Release Using Eudragit® L100 and Eudragit S100 Combinations, *Drug Develop. Indus. Pharm.*, 26(5), 549-554 (2000).

Kitano, A. et al., "Distribution and Anti-Inflammatory Effect of Mesalazine on Carrageenan-Induced Colitis in the Rabbit," *Clin. Exp. Pharmacol. Physiol.*, vol. 23, pp. 305-309, (1996).

Klotz, U. et al., "Steady State Disposition of 5-Aminosalicylic Acid Following Oral Dosing," *Arneimittelforschung*, vol. 43, No. 12, pp. 1357-1359, (1993).

Kruis et al., "The Optimal Dose of 5-Aminosalicyclic Acid in Active Ulcerative Colitis: A Dose-Finding Study With Newly Developed Mesalamine," *Clin. Gastroen. Hepat.*, vol. 1 pp. 36-43, (2003).

Lang, K. et al., "Promising New Agents for the Treatment of Inflammatory Bowel Disorders," *Drugs R&D*, vol. 1, No. 3, pp. 237-244, (1999).

Larouche, J. et al., "Release of 5-ASA from Pentasa in Patients with Crohn's Disease of the Small Intestine," *Aliment Pharm. Ther.*, vol. 9, pp. 315-320, (1995).

Lavritsen, K. et al., "Effects of Topical 5-Aminosalicylic Acid and Prednisolone on Prostaglandin $E_2$ and Leukotriene $B_4$ Levels Determined by Equilibrium In vivo Dialysis of Rectum in Relapsing Ulcerative Colitis," *Gastroenterology*, vol. 91, pp. 837-844, (1986).

Leopold, C. S., "A Practical Approach in the Design of Colon-Specific Drug Delivery Systems," Ch. 6, *Drug Targeting Organ-Specific Strategies*, Wiley-VCH Verlag GmgH, pp. 157-170, 2001.

Letter dated Oct. 4, 2007, from Innovar, L.L.C., regarding "Consideration of prior art material to patentability of claims pending in U.S. Appl. No. 10/930,743."

Levine, D. et al., "A Randomized, Double Blind, Dose-Response Comparison of Balsalazide (6.75 g), Balsalazide (2.25 g), and Mesalamine (2.4 g) in the Treatment of Active, Mild to Moderate Ulcerative Colitis," *Am. J. Gastroen.*, vol. 97, No. 6, pp. 1398-1407, (2002).

Lin, S. Y. et al., "Calcium Alginate Beads as Core Carriers of 5-Aminosalicylic Acid," *Pharm. Res.*, vol. 9, No. 9, pp. 1128-1131, (1992).

Madsen, J. R. et al., "Chronic Inflammatory Bowel Disease The Present Status" *Nordisk Medicin*, vol. 107, No. 10, pp. 254-260, (1992).

Madsen, J. et al., "The Present Status Concerning Chronic Inflammatory Bowel Disease," *Ugeskr, Laeger*, vol. 154, No. 33, pp. 2243-2250, (1992).

Mahida, Y. R. et al., "Slow-Release 5-Amino-salicylic Acid (Pentasa®) for the Treatment of Active Crohn's Disease," *Digestion*, vol. 45, pp. 88-92, (1990).

Mantzaris et al., "Budesonide Versus Mesalamine for Maintaining Remission in Patients Refusing Other Immunomodulators for Steroid-Dependent Crohn's Disease," *Clin. Gastroen. Hepat.*, vol. 1, pp. 122-128, (2003).

Marteau, P. et al., "Use of Mesalazine Slow Release Suppositories 1 g Three Times Per Week to Maintain Remission of Ulcerative Proctitis: A Randomised Double Blind Placebo Controlled Mulicentre Study," *Gut*, vol. 42, p. 195-199, (1998).

Marteau, P. et al., "Comparative Open, Randomized Trial of the Efficacy and Tolerance of Slow-Release 5-ASA Suppositories Once Daily Versus Conventional 5-ASA Suppositories Twice Daily in the Treatment of Active Cryptogenic Proctitis," *Amer. J. Gastroenterol.*, vol. 95, No. 1, pp. 166-170, (2000).

McKeage, K. et al., "Budesonide (Entocort® EC Capsules)A Review of Its Therapeutic Use in the Management of Active Crohn's Disease in Adults," *Drugs*, vol. 62, No. 15, pp. 2263-2282, (2002).

McLeod, R. S. et al., "The Release Profile of a Controlled Release Preparation of 5-Aminosalicylic Acid (Rowasa I®) in Humans," *Dis. Colon Rectum*, vol. 33, pp. 21-25, (1990).

Miner, P. et al., "Safety and Efficacy of Controlled-Release Mesalamine for Maintenance of Remission in Ulcerative Colitis," *Digest. Dis. Sci.*, vol. 40, No. 2, pp. 296-304, (1995).

Muijsers, R. et al., "Balsalazide A Review of Its Therapeutic Uses i Mild-to-Moderate Ulcerative Colitis," *Drugs*, vol. 62, No. 15, pp. 1689-1705, (2002).

Mulder, C. et al., "Double-Blind Comparison of Slow-Release 5-Aminosalicylate and Sulfasalazine in Remission Maintenance in Ulcerative Colitis," *Gastroenterology*, vol. 95, pp. 1449-1453, (1988).

Munakata, A. et al., "Double-Blind Comparative Study of Sulfasalazine and Controlled-Release Mesallazine Tablets in the Treatment of Active Ulcerative Colitis," *J. Gastroenterol.*, vol. 30, Suppl. VIII, pp. 108-111, (1995).

Ngo, Y. et al., "Efficacy of a Daily Application of Mesalazine (Pentasa)Suppository with progressive Release, in the Treatment of Ulcerative Proctitis. A Double-Blind Versus Placebo Randomized Trial," *Gastroenterol. Clin. Biol.*, vol. 16, No. 10, pp. 782-786, (1992).

Nigovic et al., "Determination of 5-Aminosalicylic Acid in Pharmaceutical Formulation by Differential Pulse Voltammetry," *J. Pharmaceut. Biomed. Anal.*, vol. 31, pp. 169-174, (2003).

Nugent et al., "Intestinal Luminal pH in Inlammatory Bowel Disease: Possible Determinants and Implications for Therapy with Aminosalicylates and Other Drugs," *Gut*, vol. 48, pp. 571-577 (2001).

Osterwald, H. P. "Pharmaceutic Development: Mesalzine," *Scan. J. Gastroentero.*, vol. 25 Suppl. 172,I.172, pp. 43-46, (1990).

Panayiotou, B. N. "Pulmonary Infiltrates and Eosinophilia Associated with Sulphasalazine Administration," *Aust. NZ J. Med.*, vol. 21, pp. 348-349, (1991).

"PENTASA® Sachet: Prolonged Release Granules 19," http://www.pentasa.com/site/ferring com/view.asp?ID=510&printmode=3, pp. 1-4, 2001.

"PENTASA® Prolonged Release Tablets, 250 & 500 mg," http://www.pentasa.com/site/ferring comlview.asp?ID=522 &printmode=3, pp. 1-4, 2001.

Prakash, A. et al., "Oral Delayed-Release Mesalazine, A Review of Its Use in Ulcerative Colitis and Crohn's Disease," *Drugs*, vol. 57, No. 3, pp. 383-408, (1999).

Prantera, C. et al., "Oral 5-Aminosalicyclic Acid (Asacol) in the Maintenance Treatment of Crohn's Disease," *Gastroenterology*, vol. 103, pp. 363-368, (1992).

Rasmussen, S. et al., "5-Aminosalicyclic Acid in a Slow-Release Preparation: Bioavailability, Plasma Level, and Excretion in Humans," *Gastroenterology*, vol. 83, pp. 1062-1070, (1982).

Rasmussen, S. N. et al., "Treatment of Crohn's Disease with Peroral 5-Aminosalicylic Acid," *Gastroenterology*, vol. 85, pp. 1350-1353, (1983).

Rasmussen, S. N. et al., "5-Aminosalicyclic Acid in the Treatment of Crohn's Disease. A 16 Week Double-Blind, Placebo-Controlled, Multicentre Study with Pentasa®," *Scan. J. Gastroentero.*, vol. 22, No. 7, pp. 877-883, (1987).

Rasmussen, S. et al., "Bioavailability of Controlled Release Mesalaizne (5-ASA) Preparations," *J. Gastroenterol.*, vol. 30, Suppl. VIII, pp. 112-114 (1995).

Resbeut, M. et al., "A Randomized Double Blind Placebo Controlled Multicenter Study of Mesalazine for the Prevention of Acute Radiation Enteritis," *Radiotherapy and Oncology*, vol. 44, No. 1, pp. 59-63, (1997).

Rijk, M. C. M. et al., "Disposition of 5-Aminosalicylic Acid by 5-Aminosalicylic Acid-Delivering Compounds," *Scan. J. Gastroentero.*, vol. 23, No. 1, pp. 107-112, (1988).

Rijk, M. C. M. et al., "Disposition of 5-Aminosalicylic Acid from 5-Amimosalicylic Acid-Delivering Drugs During Acclerated Intestinal Transit in Healthy Volunteers," *Scan. J. Gastroentero.*, vol. 24, No. 10, pp. 1179-1185, (1989).

Rijk, M. C. M. et al., "Disposition of Mesalazine form Mesalazine-Delivering Drugs in Patients with Inflammatory Bowel Disease, With and Without Diarrhoea," *Scan. J. Gastroentero.*, vol. 27, No. 10, pp. 863-868, (1992).

Riley, S. A. et al., "Comparison of Delayed-Release 5-Aminosalicylic Acid (Mesalazine) and Sulfasalazine as Maintenance Treatment for Patients With Ulcerative Colitis," *Gastroenterology*, vol. 94, pp. 1383-1389, (1988).

Riley, S. A. et al., "Comparison of Delayed Release 5 Aminosalicylic Acid (Mesalazine) and Sulphasalazine in the Treatment of Mild to Moderate Ulcerative Colitis Relapse," *Gut*, vol. 29, pp. 669-674, (1988).

Riley, S. A. et al., "Mesalazine Release from Coated Tablets: Effect of Dietary Fibre," *Br. J. Clin. Pharmac.*, vol. 32, pp. 248-250, (1991).

Rizzello, F. et al., "Oral Beclomethasone Dipropionate in Patients With Mild to Moderate Ulcerative Colitis: A Dose-Finding Study," *Advances in Therapy*, vol. 18, No. 6, pp. 261-271, (2001).

Robinson, M. et al., "Mesalamine Capsules Enhance the Quality of Life for Patients With Ulcerative Colitis," *Aliment Pharm. Ther.*, vol. 8, pp. 27-34, (1994).

Robinson, M. et al., "Medical Therapy of Inflammatory Bowel Disease for the 21$^{st}$ Century," *Eur. J. Surg.*, Suppl. 582, pp. 90-98, (1998).

Rogozina et al., "Comparative Efficacy of Mezakol and Sulfasalazine in Treating Chronic Relapsing Ulcerative Colitis," *Eksp. Klin. Gatroenterol.*, vol. 1, 58-9, 183 (2003).

Rutgeerts, P. "Conventional Treatment of Crohn's Disease: Objectives and Outcomes." *Inflamm. Bowel Dis.* vol. 7, Supp. 1, pp. S2-S8, (2001).

Sandborn, W.J. "Steroid-Dependent Crohn's Disease," *Can. J. Gastroenterol.*, vol. 14, Supp. C, pp. 17C-22C, (2000).

Sandborn, W.J. et al., "Systematic Review: the Pharmacokinetic Profiles of Oral Mesalazine Formulations and Mesalazine Pro-Drugs Used in the Management of Ulcerative Colitis," *Aliment Pharm. Ther.*, vol. 17, pp. 29-42, (2003).

Saverymuttu, S. H. et al., "Effect of a Slow-Release 5'-Aminosalicylic Acid Preparation on Disease Activity in Crohn's Disease," *Digestion*, vol. 33, pp. 89-91, (1986).

Schreiber, S. et al., "Oral 4-Aminosalicylic Acid Versus 5-Aminosalicylic Acid Slow Release Tablets. Double Blind, Controlled Pilot Study in the Maintenance Treatment of Crohn's Ilecolitis," *Gut*, vol. 35, pp. 1081-1085, (1994).

Schroeder, K.W. "Role of Mesalazine in Acute and Long-Term Treatment of Ulcerative Colitis and Its Complications," *Scan. J. Gastroentero.*, Suppl. 236 pp. 42-47, (2002).

Selby, W. S. et al., "Topical Treatment of Distal Ulcerative Colitis with 4-Amino Salicylic Acid Enemas," *Digestion*, vol. 29, pp. 231-234, (1984).

Singleton, J. et al., "Mesalamine Capsules for the Treatment of Active Crohn's Disease: Results of a 16-Week Trial," *Gastroenterology*, vol. 104, pp. 1293-1301, (1993).

Singleton, J. et al., "Quality-of-Life Results of Double-Blind, Placebo-Controlled Trial of Mesalamine in Patients with Crohn's Disease," *Digest. Dis. Sci.*, vol. 40, No. 5, pp. 931-935, (1995).

Small, R. et al., "Chemistry, Pharmacology, Pharmacokinetics, and Clinical Application of Mesalamine for the Treatment of Inflammatory Bowel Disease," *Pharmacotherapy*, vol. 14, No. 4, pp. 385-398, (1994).

Spencer, C. et al., "Budesonide A Review of its Pharmacological Properties and Therapeutic Efficacy in Inflammatory Bowel Disease," *Drugs*, vol. 50, No. 5, pp. 854-872, (1995).

Stolk, L. M. L. et al., "Dissolution Profiles of Mesalazine Formulations In Vitro," *Pharmaceutisch Weekblad Scientific Edition*, vol. 12, No. 5, pp. 200-204, (1990).

Sutherland, L. et al., "Oral 5-Aminosalicylic Acid for Induction of Remission in Ulcerative Colitis (Review)", *Cochrane Database of Systematic Reviews* 2006, Issue 2, Art. No. CD 000543.

Sutherland, L. et al., "Oral 5-Aminosalicylic Acid for Maintenance of Remission in Ulcerative Colitis (Review)," *Cochrane Database of Systematic Reviews* 2006, Issue 2, Art. No. CD 000544.

Swift et al., "A Pharmacokinetic Study of Sulphasalazine and Two New Formulations of Mesalazine," *Aliment Pharm. Ther.*, vol. 6, pp. 259-266 (1992).

Takaya, T. et al., "Importance of Dissolution Process on Systemic Availability of Drugs Delivered by Colon Delivery System," *J. Control Release*, vol. 50, pp. 111-122, (1998).

Takada, K. "DDS Preparations of Drugs for Inflammatory Bowel Disease," *Nippon Rinsho*, vol. 57, No. 11, pp. 2508-2515, (1999).

Tett, S. "Clinical Pharamcokinetics of Slow-Acting Antirheumatic Drugs," *Clin. Pharmacokinet.*, vol. 25, No. 5, pp. 392-407, (1993).

Thomsen, O. et al., "A Comparison of Budesonide and Mesalamine for Active Crohn's Disease," *N. Engl. J. Med.*, vol. 339, No. 6, pp. 370-374, (1998).

Thomsen, O. et al., "Budesonide and Mesalazine in Active Crohn's Disease: A Comparison of the Effects on Quality of Life," *Am. J. Gastroenterology*, vol. 97, No. 3, pp. 649-653, (2002).

Travis, S.P.L. et al., "Salicylates for Inflammatory Bowel Disease," *Bailliere's Clinical Gatroenterology*, vol. 8, No. 2, pp. 203-231, (1994).

Travis, S.P.L. et al., "Salicylates For Ulcerative Colitis—Their Mode of Action," *Pharmac. Ther.*, vol. 63, pp. 135-161, (1994).

Tursi et al., "Assessment of Orocaecal Transit Time in Different Localization of Crohn's Disease and its Possbile Influence on Clinical Response to Therapy," *Eur. J. Gastroen. Hepat.*, vol. 15, No. 1, pp. 69-74, (2003).

"Ulcerative Colitis (UC)—Clinical Presentation and Evolution Treatment," Asacol.com Monograph: Introduction, pp. 1-6, 2001.

Van Deventer, S.J.H. et al., "Drug Treatment of Crohn's Disease," *Ned. Tijdschr Geneeskd*, vol. 142, No. 21, pp. 1191-1195, (1998).

Vree, T.B. et al., "Liver and Gut Mucosa Acetylation of Mesalazine in Healty Volunteers," *Int. J. Clin. Pharmacol. Ther.*, vol. 38, No. 11, pp. 514-522, (2000).

Vree, T. et al., "Mono- and Biphasic Plasma Concentration-Time Curves of Mesalazine From a 500 mg Suppository in Healthy Male Volunteers Controlled by the Time of Defecation Before Dosing," *J. Pharm. Pharmacol.*, vol. 52, pp. 645-652, (2000).

Watkinson, G. "Sulphasalazine: A Review of 40 Years' Experience," *Drugs*, vol. 32, (Suppl. 1) pp. 1-11, (1986).

Wilding, I. R. et al., "Gastrointestinal Spread of Oral Prolonged-Release Mesalazine Mircogranules (Pentasa) Dosed as Either Tablets or Sachet," *Aliment Pharm. Ther.*, vol. 14, pp. 163-169, (2000).

Wilding, I. R. et al., "Combined Scintigraphic and Pharmacokinetic Investigation of Enteric-Coated Mesalazine Micropellets in Healthy Subjects," *Aliment Pharm. Ther.*, vol. 17, pp. 1153-1162, (2003).

Winther, K. et al., "Lack of Effect of 5-Aminosalicylic Acid on Platelet Aggregation and Fibrinolytic Activity In Vivo and In Vitro," *Eur. J. Clin. Pharmacol.*, vol. 33, pp. 419-422, (1987).

Yoshikawa, Y. et al., "A Dissolution Test for a Pressure-Controlled Colon Delivery Capsule: Rotating Beads Method." *J. Pharm. Pharmacol.*, vol. 51, pp. 979-989, (1999).

Yu, D.K. et al., "Pharmacokinetics of 5-Aminosalicylic Acid From Controlled-Release Capsules in Man," *Eur. J. Clin. Pharmacol.*, vol. 48, pp. 273-277, (1995).

Zambito et al., "Preparation and In Vitro Evaluation of Chitosan Matrices for Colonic Controlled Drug Delivery", *J. Pharm . Pharmaceut Sci.*, vol. 6 (2), pp. 274-281, (2003).

Zeitz, M. "Consequences of Galenic Considerations and Clinical Results with Regard to Treatment of Ulcerative Colitis," *Med. Klin.*, vol. 94 Suppl. I, pp. 41-43, (1999).

Zelissen, P. M. J. et al., "Influence of Salazosulphapyridine and 5-Aminosalicylic Acid on Seminal Qualities and Male Sex Hormones," *Scan. J. Gastroentero.*, vol. 23, No. 9, pp. 1100-1104, (1988).

Zhou, S.Y. et al., "Intestinal Metabolism and Transport of 5-Aminosalicylate," *Drug Metab. Dispos.*, vol. 27, No. 4, pp. 479-485, (1999).

Banker, G. S. et al., "Tablets," Ch. 11, *The Theory and Practice of Industrial Pharmacy*, pp. 293-345, Lea & Febriger, 1986.

Camilleri, M., et al.: "Review article: irritable bowel syndrome," *Aliment Pharm.Ther.*, vol. 11, pp. 3-15 (1997).

Dave, R. H., http://license.icopyright.net/user/viewFreeUse.act?fuid=MzcONjkyNw%3D%3D, Oct. 24, 2008 (12 pages).

Horig et al., "From bench to clinic and back: Perspective on the 1$^{st}$ IQPC Translational Research Conference," *J. Translational Medicine*, vol. 2 pp. 1-8 (2004).

International Search Report, PCT/IB2007/002029, mailed May 7, 2008.

Schafer et al., "Failure is an option: Learning from unsuccessful proof-of-concept trials," *Drug Discovery Today*, vol. 13, pp. 913-916 (2008).

Sun et al., "Transport properties of ionic drugs in the ammonio methacrylate copolymer membranes," *Pharmaceutical Research*, vol. 18, pp. 304-310 (2001).

Extended European Search Report dated Sep. 10, 2010, for European Application No. 10171069.7 (6 pages).

* cited by examiner

FORMULATIONS AND METHODS OF TREATING INFLAMMATORY BOWEL DISEASE

This application is a continuation of U.S. patent application Ser. No. 10/930,743, filed Sep. 1, 2004, now U.S. Pat. No. 7,737,133 which claims the benefit of priority of U.S. Provisional Patent Application No. 60/499,365, filed Sep. 3, 2003, both of which are incorporated herein by reference in their entireties.

This invention is directed to methods and formulations for treating inflammatory bowel disease. The methods and formulations include, but are not limited to, methods and formulations for delivering effective concentrations of 4-aminosalicylic acid and/or 5-aminosalicylic acid to affected areas of the intestine. The methods and formulations can comprise conventional and/or modified-release elements, providing for drug delivery to the affected area. Diseases and conditions treatable with the methods and formulations of the present invention include Crohn's disease and ulcerative colitis.

Gastrointestinal conditions pose a significant worldwide health problem. Inflammatory bowel diseases, which genus encompass a range of diseases including Crohn's disease and ulcerative colitis, affect nearly 1 million people in the United States each year.

The two most common inflammatory conditions of the intestine, ulcerative colitis (UC) and Crohn's disease (CD), are collectively known as inflammatory bowel disease (IBD). These conditions are diseases of the distal gut (lower small intestine, large intestine, and rectum) rather than the proximal gut (stomach and upper small intestine). Between the two, ulcerative colitis primarily affects the colon, whereas Crohn's disease affects the distal small intestine as well.

Although distinct conditions, the same drugs are commonly used to treat both UC and CD. Drugs commonly used in their treatment include steroids (for example, budesonide and other corticosteroids, and adrenal steroids such as prednisone and hydrocortisone), cytokines such as interleukin-10, antibiotics, immunomodulating agents such as azathioprine, 6-mercaptopurine, methotrexate, cyclosporine, and anti-tumor necrosis factor (TNF) agents such as soluble TNF receptor and antibodies raised to TNF, and also antinflammatory agents such as zinc. The most commonly prescribed agents for IBD include sulfasalazine (salicyl-azo-sulfapyridine, or "SASP") and related 5-aminosalicylic acid ("5-ASA") products.

It is recognized that SASP is broken down in the lower gut by colonic bacteria to yield sulfapyridine ("SP") and 5-ASA, of which 5-ASA is believed to be the primary active component. 5-ASA released in the colon is poorly absorbed and appears to act locally.

Because SP is extensively absorbed and is associated with various side effects, investigators have proposed using 5-ASA alone as a treatment for IBD. Indeed, 5-ASA, or mesalamine, has now been established as a common treatment for IBD and is widely prescribed and used for this purpose. However, 5-ASA therapy still has problems, including side effects to be detailed hereinafter. Additionally, 5-ASA exhibits an efficacy profile that is less than maximal, reflected in lower response and remission rates, and higher relapse rates, related to its site and mechanism of action.

The administration of 5-ASA is hampered by some complications associated with its delivery. For example, the compound is unstable in gastric fluids, and its extensive absorption and metabolism from the small intestine reduces its availability at distal sites in the gut, which are the sites of the therapeutic effect and the preferred sites of delivery. Ideally, the compound should reach the distal gut, but not be absorbed there. The absorption from proximal sites results in side effects associated with the absorbed drug and its systemic effects.

Existing oral 5-ASA-based therapies fall into two main categories. One involves the use of pharmaceutical dosage forms based on modified-release formulations (MR), the other is pro-drug based. In relation to dosage form-based approaches, various modified release forms have been developed and described. Both extended/sustained release formulations and delayed release formulations have been developed, with the intent of limiting 5-ASA release in the upper gut and concentrating its release in the distal gut.

For example, a sustained release formulation (PENTASA®) has been approved and used for many years. PENTASA® releases 5-ASA continuously, with approximately 50% released in the small intestine and 50% in the large intestine, and in its approved label form reports 20-30% systemic absorption. This absorption reflects the proximal release and absorption characteristics of this formulation in addition to any low level absorption from the distal gut. (See PDR datasheet for PENTASA®.) U.S. Pat. Nos. 4,496,553, 4,880,794, 4,980,173, and 5,041,431 are all directed to extended release forms of 5-ASA or its salts or esters.

U.S. Pat. No. 5,840,332 describes a GI delivery system that achieves the desired location of release of 5-ASA in the intestine through the inclusion of particulate water-insoluble material embedded in a water-insoluble coating on a drug-containing core. U.S. Pat. No. 6,004,581 describes a multi-particulate spherical-granule-containing formulation that provides for a modified and targeted release of 5-ASA, particularly to the small and large bowel. In all of these cases, however, the fundamental problems of proximal release limiting the maximum local efficacy, and resulting in significant side effects related to the systemic absorption of 5-ASA, have not been overcome.

Other approaches rely on a pH-dependent coating to achieve the desired release. For example, an enteric-coated commercial product, ASACOL®, relies on a pH-dependent acrylic-based barrier coating, which dissolves at pH values above 7, to achieve a distal 5-ASA delivery. Other examples of this type of formulation are described in U.S. Pat. Nos. 5,541,170 and 5,541,171, which describe a solid dosage form of 5-ASA, or its salts or esters, that achieves delivery to the large intestine through a coating that is insoluble in gastric and intestinal conditions (less than pH 7) but soluble in the colon (pH greater than 7).

The drawback of formulations such as these is that the regional gut pH can vary significantly from one person to the next, and can be influenced by the presence of food, or other conditions. In fact, diseases such as IBD can themselves cause intestinal pH to vary. The package information for ASACOL® states that its systemic absorption is as high as 28%. Because absorption is generally occurring only in the small intestine, the relatively high systemic absorption suggests a significant variability in ASACOL®'s site of release.

In general, pH-dependent systems for targeting 5-ASA release to a specific location in the intestine can be unreliable for a number of reasons. For example, premature release and associated systemic absorption may result from a proximal intestinal pH at or above the critical triggering pH. Alternatively, incomplete or minimal release may result from the occurrence of the critical pH at a site distal of the affected area. Nugent et al., *Gut* 48, pages 571-577 (2001), reviews the potential problems of the pH-dependent distal gut delivery approach, pointing out that the existence of inter-subject variations in intestinal pH. These problems have led to proposed improvements in targeting the delivery of 5-ASA to the distal gut.

U.S. Pat. No. 5,716,648 describes an oral composition that relies on a pH-dependent soluble coating, but also includes a pH-regulating alkaline material to attempt to compensate for patients with "subnormal intestinal pH." Other approaches include those described in U.S. Pat. No. 5,866,619, which is generally directed to a non-pH-dependent colonic drug-delivery system involving a saccharide-containing polymer, which is enzymatically degraded by the colon. Another example is provided by U.S. Pat. No. 6,506,407, which generally describes a colon-specific drug-releasing system that combines a pH-dependent outer coating with the inclusion of a saccharide substrate, which upon enzymatic breakdown by enterobacteria produces an organic acid that subsequently dissolves an acid-soluble inner coating.

Still other examples are described in U.S. Application No. 2002/0098235, which describes the use of multiple pH-dependent coatings to reduce the impact of coating fractures. U.S. Application No. 2001/0055616 describes a pellet formulation for treating intestinal tract conditions, which utilizes a pH-dependent enteric coating to target release from a non-gel-forming drug-containing polymeric matrix core. U.S. Application 2001/0036473 describes a pH-dependent coating on a hydroxypropylmethylcellulose capsule for enteric and colonic delivery. And U.S. Application No. 2001/0026807 describes various coatings, including pH-dependent materials, redox-sensitive materials, and materials subject to breakdown by bacteria, on a starch capsule to achieve colonic delivery.

Despite the descriptions of proposed improvements in these documents, a colonic 5-ASA-delivery system that does not suffer from the variability in inter-subject intestinal pH is still not commercially available. Thus, the inherent difficulties in 5-ASA delivery have yet to be solved in a commercially acceptable manner.

A compound related to, but more stable than 5-ASA, is 4-ASA, also known as para-aminosalicylic acid. Like 5-ASA, 4-ASA is effective in treating IBD, although it has never been approved in oral form for such a use. It has been approved for use in certain European countries as a rectal enema, i.e., QUADRAS® by Norgine.

4-ASA has been used as an oral preparation since the 1940s as a treatment for tuberculosis (TB). Para-aminosalicylic acid has certain advantages over 5-ASA in treating IBD. In addition to its higher aqueous stability, it reportedly exhibits an absence of nephrotoxicity, and extensive experience and use at daily doses as high as 8 g in the treatment of TB has demonstrated its safety. (Ginsberg et al., *Gastroenterology* 102, 448-452, 1998.)

As an approved form for use in TB, 4-ASA is commonly presented as an enteric formulation in order to minimize the degradation of the drug in the stomach. Modified release oral dosage forms of 4-ASA for use in TB have also been described. Because absorption of the 4-ASA is important in TB treatment, such formulations are designed to maximize 4-ASA absorption.

Unlike the situation with 5-ASA, modified-release oral dosage forms of 4-ASA for use in IBD have not been widely described. U.S. Pat. No. 5,716,648 does describe an oral composition for 4-ASA in treating IBD. However, this disclosure is directed specifically to pharmaceutical oral compositions that include a pH regulating alkaline material to deal with subnormal gut pH.

In addition to targeting IBD with modified-release 5-ASA products, IBD has been targeted with pro-drugs that are self-targeting. For example, olsalazine, which is formed from two molecules of 5-ASA linked by an azo-bond (5,5'-azo-bis salicylic acid), naturally targets the colon. It is stable in gastric conditions, thus able to bypass the stomach, and is minimally absorbed intact from the gut (2.4%). But it is rapidly converted to two molecules of 5-ASA in the colon through the action of colonic bacteria. This mechanism inherently delivers 5-ASA to the desired site of action. The marketed form of olsalazine, DIPENTUM®, is a simple non-modified-release powder-filled capsule.

The problem with this formulation is that the entire dose is exposed to the action of the intestinal enzymes upon entering the colon. Thus, upon entering the colon, all of the olsalazine is cleaved into 5-ASA, essentially providing a bolus dose to a concentrated area in the proximal colon. After a fairly substantial absorption (approximately 20%), the remainder of the bolus dose is then left to diffuse throughout the colon, without any control as to where it is directed.

Because olsalazine is self-targeting to the colon, there has been little focus on modified release forms of olsalazine or other bis-azo ASA pro-drug forms. U.S. Patent Application No. 2002/0192282 describes a multilayer pharmaceutical formulation for release of various drugs, including olsalazine, in the colon and includes a pH-dependent outer coating layer. The problem with such a formulation was described above with respect to other pH-dependent formulations: because of the potential variability in the pH of the gut, these systems may not properly release at affected sites due to distal gut pH values below the critical value.

U.S. Pat. No. 4,374,932 describes a drug delivery system for 5,5'-azo-bis salicylic acid designed to bypass absorption of the 5,5'-azo-bis salicylic acid entity in the stomach and small intestine, and utilizes an ion-exchange complex of diacidic 5,5'-azo-bis salicylic acid and an anionic exchange resin. However, the absorption of olsalazine from the conventional powder capsule already results in only 2.4% absorption, and thus this formulation does not provide an important therapeutic advantage.

In view of the foregoing, there remains a need in the art for methods and pharmaceutical formulations that can be used to deliver 4-ASA and/or 5-ASA in therapeutically effective concentrations to affected areas of the gastrointestinal tract. The present invention solves the problems identified in the art, and provides such methods and formulations.

This invention is advantageous in providing methods and formulations for treating inflammatory bowel disease.

The invention has the advantage of delivering effective concentrations of 4-ASA and/or 5-ASA to affected areas of the gastrointestinal tract, with minimized systemic absorption.

The invention is directed to, among other things, disodium 4,4'-azo-bis salicylate. The invention is also directed to pharmaceutical compositions comprising 4,4'-azo-bis salicylic acid, or a pharmaceutically acceptable salt thereof, and at least one pharmaceutically acceptable excipient. In some embodiments, the pharmaceutically acceptable salt thereof comprises disodium 4,4'-azo-bis-salicylate. In some embodiments, the pharmaceutically acceptable excipient is chosen from carriers, fillers, extenders, binders, humectants, disintegrating agents, solution-retarding agents, absorption accelerators, wetting agents, absorbents, lubricants, stabilizers, coloring agents, buffering agents, dispersing agents, preservatives, organic acids, and organic bases.

The invention is also directed to pharmaceutical compositions comprising: a salicylate and/or salicylic acid chosen from 4-amino salicylic acid, 5-amino salicylic acid, pharmaceutically acceptable salts thereof, and pro-drugs thereof, and at least one pharmaceutically acceptable excipient, formulated as a modified-release pharmaceutical composition, wherein the composition exhibits a delay in release that is dependent on surrounding pH.

The pharmaceutical composition may exhibit the following dissolution profile, when tested in a U.S.P. Type II apparatus (paddles) at 37° C. and 50 rpm, in 0.01N HCl for two hours followed by pH 6.8 buffer for the remainder of the test: 1 hour (in 0.01N HCl): from about 0 to about 10% drug released; 2 hours (in 0.01N HCl): from about 0 to about 10% drug released; 1 hour (in pH 6.8): from about 10 to about 35% drug released; 2 hours (in pH 6.8): from about 20 to about 65% drug released; 4 hours (in pH 6.8): from about 55 to about 95% drug released; 6 hours (in pH 6.8): from about 90 to about 100% drug released; and 12 hours (in pH 6.8): about 90% or greater drug released. In some embodiments, the composition exhibits the following dissolution profile, when tested in a U.S.P. Type II apparatus (paddles) at 37° C. and 50 rpm, in 0.01N HCl for two hours followed by pH 6.8 buffer for the remainder of the test: 1 hour (in 0.01N HCl): from about 0 to about 5% drug released; 2 hours (in 0.01N HCl): from about 0 to about 5% drug released; 1 hour (in pH 6.8): from about 15 to about 30% drug released; 2 hours (in pH 6.8): from about 25 to about 60% drug released; 4 hours (in pH 6.8): from about 60 to about 90% drug released; 6 hours (in pH 6.8): from about 90 to about 100% drug released; and 12 hours (in pH 6.8): about 95% or greater drug released.

The present invention is also directed to pharmaceutical compositions comprising: a salicylate and/or salicylic acid chosen from 4-amino salicylic acid, 5-amino salicylic acid, pharmaceutically acceptable salts thereof, and pro-drugs thereof, and at least one pharmaceutically acceptable excipient, formulated as a modified-release pharmaceutical composition, wherein the composition exhibits a drug-release profile that is independent of surrounding pH.

The composition may exhibit the following dissolution profile, when tested in a U.S.P. Type II apparatus (paddles) at 37° C. and 50 rpm, in pH 6.8 buffer for the test: 1 hour: less than or equal to about 10% drug released; 2 hours: from about 0 to about 35% drug released; 3 hours: from about 10 to about 60% drug released; 4 hours: from about 20 to about 60% drug released; 6 hours: from about 40 to about 80% drug released; and 12 hours: from about 75 to about 100% drug released. In some embodiments, the composition exhibits the following dissolution profile, when tested in a U.S.P. Type II apparatus (paddles) at 37° C. and 50 rpm, in pH 6.8 buffer for the test: 1 hour: less than or equal to about 5% drug released; 2 hours: from about 0 to about 25% drug released; 3 hours: from about 15 to about 30% drug released; 4 hours: from about 40 to about 50% drug released; 6 hours: from about 60 to about 75% drug released; and 12 hours: from about 90 to about 100% drug released.

The modified-release compositions of the invention may comprise an immediate-release core and a semi-permeable membrane. In some embodiments, the modified-release compositions of the invention may comprise a modified-release matrix core and a semi-permeable membrane. In some embodiments, the salicylate and/or salicylic acid is chosen from 4-aminosalicylic acid and 5-aminosalicylic acid, or at least one pharmaceutically acceptable salt or ester thereof. In some embodiments, the composition comprises 4-aminosalicylic acid and 5-aminosalicylic acid, or pharmaceutically acceptable salts or esters thereof. In some embodiments, the salicylate and/or salicylic acid is chosen from 5,5'-azo-bis salicylic acid, 4,5'-azo-bis salicylic acid, 4,4'-azo-bis salicylic acid, and pharmaceutically acceptable salts thereof.

The invention also includes methods of treating inflammatory bowel disease comprising administering an effective amount of 4,4'-azo-bis salicylic acid to a subject in need of such treatment. The method may include administering 4,4'-azo-bis salicylic acid in a modified-release formulation. In some embodiments, the modified-release formulation exhibits a release profile with delayed-release and extended-release properties.

The foregoing and other objects, features, and advantages of the invention will be apparent from the following more particular description of various embodiments of the invention. It is to be understood that both the foregoing general description and the following more detailed description are exemplary and explanatory only and are not restrictive of the invention, as claimed.

This invention relates to formulations and methods for treating inflammatory bowel disease. The term "inflammatory bowel disease" includes, but is not limited to, ulcerative colitis and Crohn's disease. Other diseases contemplated for treatment or prevention by the present invention include non-ulcerative colitis, and carcinomas, polyps, and/or cysts of the colon and/or rectum. All of these diseases fall within the scope of the term "inflammatory bowel disease" as used in this specification, yet the invention does not require the inclusion of each recited member. Thus, for example, the invention may be directed to the treatment of Crohn's disease, to the exclusion of all the other members; or to ulcerative colitis, to the exclusion of all the other members; or to any single disease or condition, or combination of diseases or conditions, to the exclusion of any other single disease or condition, or combination of diseases or conditions.

The inventive formulations and methods provide for the delivery of effective concentrations of 4-ASA and/or 5-ASA to the desired or affected area, e.g., the distal small intestine and/or colon, of the intestinal tract. The invention includes modified-release formulations of 4-ASA and/or 5-ASA, including formulations that exhibit delayed- and/or extended-release characteristics.

In other embodiments, formulations include a "pro-drug" of 4-ASA and/or 5-ASA. As used herein, the term "pro-drug" means any compound or composition that yields an active agent at some point following administration. Thus, for example, a pro-drug of 4-ASA is one that yields 4-ASA; a pro-drug of 5-ASA, or a 5-ASA pro-drug, is one that yields 5-ASA. There is no requirement that the pro-drug itself be inactive—in some instances the pro-drug can be active, and yet still yield a different active agent. There is also no requirement that a pro-drug yield only one active agent—a pro-drug may yield two or more active agents, and the yielded agents may be the same or different. Examples of pro-drugs useful in accordance with this invention include, but are not limited to, sulfasalazine, which yields 5-ASA in the colon, and olsalazine, which comprises two molecules of 5-ASA linked by an azo-bond, i.e., 5,5'-azo-bis-salicylic acid, and yields two molecules of 5-ASA.

Olsalazine, as discussed above, has the advantage of being stable in gastric conditions and being minimally absorbed intact from the gut (2.4%). Olsalazine is rapidly converted to two molecules of 5-ASA in the colon through the action of colonic bacteria. This is the same mechanism by which 5-ASA is formed from sulfasalazine in the colon.

The modified-release formulations of the current invention are directed to modifying the release of, for example, olsalazine so that the cleavage of 5-ASA from olsalazine occurs at a slow and controlled manner. The advantage of this new approach is that it reduces the rapid and extensive conversion of olsalazine to 5-ASA by the action of the colonic bacteria and the low prevailing redox potential. Whereas DIPENTUM® (commercially available form of olsalazine) results in a high local concentration of 5-ASA in the distal gut, resulting in systemic absorption of 5-ASA or its acetylated form (approximately 20%), the modified-release formulations of the current invention, by regulating the rate at which the pro-drug is made available for conversion and thereby for formation of the active moiety, overcome these problems and provide for a safer and more effective form.

In addition to olsalazine, the present invention is also directed to the use of 4,5'-azo-bis salicylic acid, described in U.S. Pat. No. 4,591,584, which is converted in the distal gut to both 4-ASA and 5-ASA. Also included within the scope of this invention is 4,4'-azo-bis salicylic acid, which has not been described previously as an agent for treating IBD. This form will be converted exclusively to 4-ASA and can be administered in both un-modified and modified-release forms. Modified-release formulations of 5,5' azo-bis, 5,4' azo-bis, 4,4' azo-bis, and combinations thereof, are also within the scope of this invention. In fact, the inventors expressly contemplate the use of any pro-drugs that yield 4-ASA and/or 5-ASA.

In this regard, reference is made to U.S. Pat. No. 6,602,915, directed to therapeutic azo-compounds for drug delivery. This patent is generally directed to polymers of azo-compounds, including polymers of azo-linked 4-ASA and polymers of azo-linked 5-ASA. The use of such polymers, and formulations containing them, is within the scope of the present invention.

Balsalazide is a commercially available pro-drug of 5-ASA that is cleaved in the colon to release 5-ASA together with a largely unabsorbed and inert moiety, 4-aminobenzoyl-beta-alanine. U.S. Pat. No. 6,458,776 describes a derivative of 5-ASA that, upon reduction of the azo bond in the colon, releases both 5-ASA and a non-absorbable antibiotic. These pro-drug compounds are also within the scope of the present invention, and can be formulated as modified-release formulations according to the invention.

Indeed, the present invention is not limited to any of the particular azo-bis compounds described herein. The present invention extends to the use and formulation of any azo-bis compound that yields either 4-ASA and/or 5-ASA. Modified-release formulations of any such azo-bis compound are specifically contemplated. Thus, as used herein in association with the present invention, the term "drug" refers to compounds useful in treating IBD or other diseases according to this invention, including but not limited to SASP, 5-ASA, and/or 4-ASA; the term "pro-drug" refers to any compound that yields such drugs, including but not limited to olsalazine, balzalazine, and/or any other azo-containing compound that yields such drug or drugs.

As used herein, the term "modified-release" formulation or dosage form includes pharmaceutical preparations that achieve a desired release of the drug from the formulation. A modified-release formulation can be designed to modify the manner in which the active ingredient is exposed to the desired target. For example, a modified-release formulation can be designed to focus the delivery of the active agent entirely in the distal large intestine, beginning at the cecum, and continuing through the ascending, transverse, and descending colon, and ending in the sigmoid colon. Alternatively, for example, a modified-release composition can be designed to focus the delivery of the drug in the proximal small intestine, beginning at the duodenum and ending at the ileum. In still other examples, the modified-release formulations can be designed to begin releasing active agent in the jejunum and end their release in the transverse colon. The possibilities and combinations are numerous, and are clearly not limited to these examples.

The term "modified-release" encompasses "extended-release" and "delayed-release" formulations, as well as formulations having both extended-release and delayed-release characteristics. An "extended-release" formulation can extend the period over which drug is released or targeted to the desired site. A "delayed-release" formulation can be designed to delay the release of the pharmaceutically active compound for a specified period. Such formulations are referred to herein as "delayed-release" or "delayed-onset" formulations or dosage forms. Modified-release formulations of the present invention include those that exhibit both a delayed- and extended-release, e.g., formulations that only begin releasing after a fixed period of time or after a physicochemical change has occurred, for example, then continue releasing over an extended period.

As used herein, the term "immediate-release formulation," is meant to describe those formulations in which more than about 50% of active ingredient is released from the dosage form in less than about 2 hours. Such formulations are also referred to herein as "conventional formulations."

The formulations of the present invention are intended to include formulations that are generic to treating all forms of IBD, and thus target their contents to both the distal small intestine and the large intestine. Other formulations within the scope of the invention include those that are more specifically designed for treating a specific disease. For example, a formulation for treating ulcerative colitis can be designed to deliver its contents entirely to the colon.

The formulations of the present invention can exist as multi-unit or single-unit formulations. The term "multi-unit" as used herein means a plurality of discrete or aggregated particles, beads, pellets, granules, tablets, or mixtures thereof, for example, without regard to their size, shape, or morphology. Single-unit formulations include, for example, tablets, caplets, and pills.

The methods and formulations of the present invention are intended to encompass all possible combinations of components that exhibit modified-release and immediate-release properties. For example, a formulation and/or method of the invention can contain components that exhibit extended-release and immediate-release properties, or both delayed-release and immediate-release properties, or both extended-release and delayed-release properties, or a combination of all three properties. For example, a multiparticulate formulation including both immediate-release and extended-release components can be combined in a capsule, which is then coated with an enteric coat to provide a delayed-release effect. Or, for example, a delayed- and extended-release caplet may comprise a plurality of discrete extended-release particles held together with a binder in the caplet, which is coated with an enteric coating to create a delay in dissolution.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566.

A number of modified dosage forms suitable for use are described below. A more detailed discussion of such forms can also be found in, for example *The Handbook of Pharmaceutical Controlled Release Technology*, D. L. Wise (ed.), Marcel Decker, Inc., New York (2000); and also in *Treatise on*

*Controlled Drug Delivery: Fundamentals, Optimization, and Applications*, A. Kydonieus (ed.), Marcel Decker, Inc., New York, (1992), the relevant contents of each of which are hereby incorporated by reference for this purpose. Examples of modified-release formulations include but are not limited to, membrane-modified, matrix, osmotic, and ion-exchange systems. All of these can be in the form of single-unit or multi-unit dosage forms, as alluded to above.

With membrane-modified extended-release dosage forms, a semi-permeable membrane can surround the formulation containing the active substance of interest. Semi-permeable membranes include those that are permeable to a greater or lesser extent to both water and solute. This membrane can include water-insoluble and/or water-soluble polymers, and can exhibit pH-dependent and/or pH-independent solubility characteristics. Polymers of these types are described in detail below. Generally, the characteristics of the polymeric membrane, which may be determined by, e.g., the composition of the membrane, will determine the nature of release from the dosage form.

Matrix-Based Dosage Forms

Matrix-type systems comprise an active substance of interest, mixed with either water-soluble, e.g., hydrophilic polymers, or water-insoluble, e.g., hydrophobic polymers. Generally, the properties of the polymer used in a modified-release dosage form will affect the mechanism of release. For example, the release of the active ingredient from a dosage form containing a hydrophilic polymer can proceed via both surface diffusion and/or erosion. Mechanisms of release from pharmaceutical systems are well known to those skilled in the art. Matrix-type systems can also be monolithic or multiunit, and can be coated with water-soluble and/or water-insoluble polymeric membranes, examples which are described above.

Matrix formulations of the present invention can be prepared by using, for example, direct compression or wet granulation. A functional coating, as noted above, can then be applied in accordance with the invention. Additionally, a barrier or sealant coat can be applied over a matrix tablet core prior to application of a functional coating. The barrier or sealant coat can serve the purpose of separating an active ingredient from a functional coating, which can interact with the active ingredient, or it can prevent moisture from contacting the active ingredient. Details of barriers and sealants are provided below.

In a matrix-based dosage form in accordance with the present invention, the drug and/or pro-drug and optional pharmaceutically acceptable excipient(s) are dispersed within a polymeric matrix, which typically comprises one or more water-soluble polymers and/or one or more water-insoluble polymers. The drug can be released from the dosage form by diffusion and/or erosion. Wise and Kydonieus describe such matrix systems in detail.

Suitable water-soluble polymers include, but are not limited to, polyvinyl alcohol, polyvinylpyrrolidone, methylcellulose, hydroxypropylcellulose, hydroxypropylmethylcellulose, or polyethylene glycol, and/or mixtures thereof.

Suitable water-insoluble polymers also include, but are not limited to, ethylcellulose, cellulose acetate, cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride) or polyurethane, and/or mixtures thereof.

Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, EXPLOTAB™, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients can have more than one role or function, or can be classified in more than one group; the classifications are descriptive only, and are not intended to limit any use of a particular excipient.

In one example, a matrix-based dosage form can comprise the drug or pro-drug, a filler, such as starch, lactose, or microcrystalline cellulose (AVICEL™); a binder/controlled-release polymer, such as hydroxypropyl methylcellulose or polyvinyl pyrrolidone; a disintegrant, such as EXPLOTAB™, crospovidone, or starch; a lubricant, such as magnesium stearate or stearic acid; a surfactant, such as sodium lauryl sulfate or polysorbates; and a glidant, such as colloidal silicon dioxide (AEROSIL™) or talc.

The amounts and types of polymers, and the ratio of water-soluble polymers to water-insoluble polymers in the inventive formulations are generally selected to achieve a desired release profile of the drug or pro-drug, as described below. For example, by increasing the amount of water insoluble-polymer relative to the amount of water soluble-polymer, the release of the drug can be delayed or slowed. This is due, in part, to an increased impermeability of the polymeric matrix, and, in some cases, to a decreased rate of erosion during transit through the gastrointestinal tract.

Of course, matrix-based dosage forms may be coated with a diffusion-control membrane, such as a semi-permeable or selectively permeable membrane. Indeed, many of the formulation components described herein can be used in combination: instant release cores with diffusion-controlled membranes or matrix cores with diffusion-controlled membranes, for example.

Osmotic Pump Dosage Forms

In another embodiment, the modified-release formulations of the present invention are provided as osmotic pump dosage forms. In an osmotic pump dosage form, a core containing drug or pro-drug and optionally one or more osmotic excipients is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form can contain two internal compartments in the core. The first compartment contains the drug and the second compartment can contain a polymer, which swells on contact with aqueous fluid. After ingestion, this polymer swells into the drug-containing compartment, diminishing the volume occupied by the drug, thereby forcing the drug from the device at a controlled rate over an extended period of time. Such dosage forms are often used when a zero order release profile is desired.

Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. Osmotic pumps of the present invention can be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

One or more delivery orifices can be drilled through the selectively permeable membrane wall. Alternatively, one or more orifices in the wall can be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice, as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), cellulose acetate, cellulose diacetate, cellulose triacetate, and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, D-mannitol, urea, sorbitol, inositol, raffinose, sucrose, glucose, hydrophilic polymers such as cellulose polymers, and/or mixtures thereof.

As discussed above, the osmotic pump dosage form can contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as to increase the hydrostatic pressure within the dosage form. The polymers can swell or expand to a very high degree, usually exhibiting a 2- to 50-fold volume increase. The polymers can be non-cross-linked or cross-linked. In one embodiment, the swellable polymers are hydrophilic polymers.

Suitable polymers include, but are not limited to, poly (hydroxy alkyl methacrylate) having a molecular weight of from 30,000 to 5,000,000; kappa-carrageenan; polyvinylpyrrolidone having a molecular weight of from 10,000 to 360,000; anionic and cationic hydrogels; polyelectrolyte complexes; poly (vinyl alcohol) having low amounts of acetate, cross-linked with glyoxal, formaldehyde, or glutaraldehyde, and having a degree of polymerization from 200 to 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene or isobutylene; water-swellable polymers of N-vinyl lactams; and/or mixtures of any of the foregoing.

The term "orifice" as used herein comprises means and methods suitable for releasing the drug from the dosage form. The expression includes one or more apertures or orifices that have been bored through the selectively permeable membrane by mechanical procedures. Alternatively, an orifice can be formed by incorporating an erodible element, such as a gelatin plug, in the selectively permeable membrane. In such cases, the pores of the selectively permeable membrane form a "passageway" for the passage of the drug. Such "passageway" formulations are described, for example, in U.S. Pat. Nos. 3,845,770 and 3,916,899, the relevant disclosures of which are incorporated herein by reference for this purpose.

The osmotic pumps useful in accordance with this invention can be manufactured by known techniques. For example, the drug and other ingredients can be milled together and pressed into a solid having the desired dimensions (e.g., corresponding to the first compartment). The swellable polymer is then formed, placed in contact with the drug, and both are surrounded with the selectively permeable agent. If desired, the drug component and polymer component can be pressed together before applying the selectively permeable membrane. The selectively permeable membrane can be applied by any suitable method, for example, by molding, spraying, or dipping.

Membrane-Modified Dosage Forms

The modified-release formulations of the present invention can also be provided as membrane modified formulations. Membrane-modified formulations of the present invention can be made by preparing a rapid release core, which can be a monolithic (e.g., tablet) or multi-unit (e.g., pellet) type, and coating the core with a membrane. The membrane-modified core can then be further coated with a functional coating. In between the membrane-modified core and functional coating, a barrier or sealant can be applied. Details of membrane-modified dosage forms are provided below.

For example, the drug or pro-drug can be provided in a multiparticulate membrane-modified formulation. The drug or pro-drug can be formed into an active core by applying the compound to a nonpareil seed having an average diameter in the range of about 0.4 to about 1.1 mm, or about 0.85 to about 1 mm. The drug or pro-drug can be applied with or without additional excipients onto the inert cores, and can be sprayed from solution or suspension using a fluidized bed coater (e.g., Wurster coating) or pan coating system. Alternatively, the drug or pro-drug can be applied as a powder onto the inert cores using a binder to bind the drug or pro-drug onto the cores. Active cores can also be formed by extrusion of the core with suitable plasticizers (described below) and any other processing aids as necessary.

The modified-release formulations of the present invention comprise at least one polymeric material, which can be applied as a membrane coating to the drug-containing cores. Suitable water-soluble polymers include, but are not limited to, polyvinyl alcohol, polyvinylpyrrolidone, methylcellulose, hydroxypropylcellulose, hydroxypropylmethyl cellulose, or polyethylene glycol, and/or mixtures thereof.

Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride), or polyurethane, and/or mixtures thereof.

EUDRAGIT™ polymers (available from Rohm Pharma) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers which are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

In one embodiment comprising a membrane-modified dosage form, the polymeric material comprises methacrylic acid co-polymers, ammonio methacrylate co-polymers, or a mixture thereof. Methacrylic acid co-polymers such as EUDRAGIT™ S and EUDRAGIT™ L (Rohm Pharma) are particularly suitable for use in the modified-release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit a solubility at a pH between the pHs at which EUDRAGIT™ L and EUDRAGIT™ S are separately soluble.

The membrane coating can comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water-insoluble polymers. Alternatively, the membrane coating can comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

Ammonio methacrylate co-polymers such as Eudragit RS and Eudragit RL (Rohm Pharma) are suitable for use in the modified-release formulations of the present invention. These polymers are insoluble in pure water, dilute acids, buffer solutions, or digestive fluids over the entire physiological pH range. The polymers swell in water and digestive fluids independently of pH. In the swollen state they are then permeable to water and dissolved actives. The permeability of the polymers depends on the ratio of ethylacrylate (EA), methyl methacrylate (MMA), and trimethylammonioethyl methacrylate chloride (TAMCl) groups in the polymer. Those polymers having EA:MMA:TAMCl ratios of 1:2:0.2 (Eudragit RL) are more permeable than those with ratios of 1:2:0.1 (Eudragit RS). Polymers of Eudragit RL are insoluble polymers of high permeability. Polymers of Eudragit RS are insoluble films of low permeability.

The ammonio methacrylate co-polymers can be combined in any desired ratio. For example, a ratio of Eudragit RS:Eudragit RL (90:10) can be used. The ratios can furthermore be adjusted to provide a delay in release of the drug or pro-drug. For example, the ratio of Eudragit RS:Eudragit RL can be about 100:0 to about 80:20, about 100:0 to about 90:10, or any ratio in between. In such formulations, the less permeable polymer Eudragit RS would generally comprise the majority of the polymeric material.

The ammonio methacrylate co-polymers can be combined with the methacrylic acid co-polymers within the polymeric material in order to achieve the desired delay in release of the drug or pro-drug. Ratios of ammonio methacrylate co-polymer (e.g., Eudragit RS) to methacrylic acid co-polymer in the range of about 99:1 to about 20:80 can be used. The two types of polymers can also be combined into the same polymeric material, or provided as separate coats that are applied to the core.

In addition to the Eudragit polymers described above, a number of other such copolymers can be used to control drug release. These include methacrylate ester co-polymers (e.g., Eudragit NE 30D). Further information on the Eudragit polymers can be found in "Chemistry and Application Properties of Polymethacrylate Coating Systems," in *Aqueous Polymeric Coatings for Pharmaceutical Dosage Forms* (ed. James McGinity, Marcel Dekker Inc., New York, pg 109-114).

The coating membrane can further comprise one or more soluble excipients so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose and sucrose, sugar alcohols such as lactitol, maltitol, mannitol, sorbitol and xylitol, xanthan gum, dextrins, and maltodextrins. In some embodiments, polyvinyl pyrrolidone, mannitol, and/or polyethylene glycol can be used as soluble excipients. The soluble excipient(s) can be used in an amount of from about 0.5% to about 80% by weight, based on the total dry weight of the polymer.

In another embodiment, the polymeric material comprises one or more water-insoluble polymers, which are also insoluble in gastrointestinal fluids, and one or more water-soluble pore-forming compounds. For example, the water-insoluble polymer can comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds can be uniformly or randomly distributed throughout the water-insoluble polymer. Typically, the pore-forming compounds comprise about 1 part to about 35 parts for each about 1 to about 10 parts of the water-insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane can also be coated with an enteric coating, as described herein, to inhibit release in the stomach.

For example, a pore forming modified release dosage form can comprise drug or pro-drug; a filler, such as starch, lactose, or microcrystalline cellulose (AVICEL™); a binder/modified release polymer, such as hydroxypropyl methylcellulose or polyvinyl pyrrolidone; a disintegrant, such as, EXPLOTAB™, crospovidone, or starch; a lubricant, such as magnesium stearate or stearic acid; a surfactant, such as sodium lauryl sulfate or polysorbates; and a glidant, such as colloidal silicon dioxide (AEROSIL™) or talc.

The polymeric material can also include one or more auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 0.5% to about 300% by weight, and can range from about 0.5% to about 100%, based on the total dry weight of the polymer. In one embodiment, talc is the filler.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 0.5% to about 50%, for example, about 0.5, 1, 2, 5, 10, 20, 30, 40, or 50%, based on the weight of the dry polymer.

Anti-foaming agents can also be included. In one embodiment, the anti-foaming agent is simethicone. The amount of anti-foaming agent used typically comprises from about 0% to about 0.5% of the final formulation.

The amount of polymer to be used in the membrane modified formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 0.5% to about 100% weight gain to the cores. In one embodiment, the weight gain from the polymeric material ranges from about 2% to about 70%.

The combination of all solid components of the polymeric material, including co-polymers, fillers, plasticizers, and optional excipients and processing aids, typically provides an about 0.5% to about 450% weight gain on the cores. In one embodiment, the weight gain is about 2% to about 160%.

The polymeric material can be applied by any known method, for example, by spraying using a fluidized bed coater (e.g., Wurster coating) or pan coating system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at any temperature above room temperature.

A sealant or barrier can also be applied to the polymeric coating. A sealant or barrier layer can also be applied to the core prior to applying the polymeric material. A sealant or barrier layer is not intended to modify the release of drug or pro-drug. Suitable sealants or barriers are permeable or soluble agents such as hydroxypropyl methylcellulose, hydroxypropyl cellulose, hydroxypropyl ethylcellulose, and xanthan gum.

Other agents can be added to improve the processability of the sealant or barrier layer. Such agents include talc, colloidal silica, polyvinyl alcohol, titanium dioxide, micronized silica, fumed silica, glycerol monostearate, magnesium trisilicate and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000 and OPADRY OY/B/28920 WHITE, each of which is available from Colorcon Limited, England.

The invention also provides an oral dosage form containing a multiparticulate drug or pro-drug formulation as hereinabove defined, in the form of caplets, capsules, particles for suspension prior to dosing, sachets, or tablets. When the dosage form is in the form of tablets, the tablets can be disintegrating tablets, fast dissolving tablets, effervescent tablets, fast melt tablets, and/or mini-tablets. The dosage form can be of any shape suitable for oral administration of a drug, such as spheroidal, cube-shaped, oval, or ellipsoidal. The dosage forms can be prepared from the multiparticulates in any known manner and can include additional pharmaceutically acceptable excipients.

All of the particular embodiments described above, including but not limited to, matrix-based, osmotic pump-based, soft gelatin capsules, and/or membrane-modified forms, which can further take the form of monolithic and/or multi-unit dosage forms, can have a functional coating. Such coatings generally serve the purpose of delaying the release of the drug for a predetermined period. For example, such coatings can allow the dosage form to pass through the stomach without being subjected to stomach acid or digestive juices. Thus, such coatings can dissolve or erode upon reaching a desired point in the gastrointestinal tract, such as the upper intestine.

Such functional coatings can exhibit pH-dependent or pH-independent solubility profiles. Those with pH-independent profiles generally erode or dissolve away after a predetermined period, and the period is generally directly proportional to the thickness of the coating. Those with pH-dependent profiles, on the other hand, can maintain their integrity while in the acid pH of the stomach, but quickly erode or dissolve upon entering the more basic upper intestine.

Thus, a matrix-based, osmotic pump-based, or membrane-modified formulation can be further coated with a functional coating that delays the release of the drug. For example, a membrane-modified formulation can be coated with an enteric coating that delays the exposure of the membrane-modified formulation until the upper intestine is reached. Upon leaving the acidic stomach and entering the more basic intestine, the enteric coating dissolves. The membrane-modified formulation then is exposed to gastrointestinal fluid, and releases drug or pro-drug over an extended period, in accordance with the invention. Examples of functional coatings such as these are known in the art.

The thickness of the polymer in the formulations, the amounts and types of polymers, and the ratio of water-soluble polymers to water-insoluble polymers in the modified-release formulations are generally selected to achieve a desired release profile of drug or pro-drug. For example, by increasing the amount of water-insoluble-polymer relative to the water-soluble polymer, the release of the drug can be delayed or slowed.

Immediate-release formulations according to the present invention, when measured by a U.S. Pharmacopoeia (USP) Type 1 Apparatus (baskets) or U.S. Pharmacopeia (USP) Type 2 Apparatus (paddles) at 37° C. and 50 rpm or higher in phosphate buffer at pH 6.8 or higher for the measuring period, can exhibit the following dissolution profile: about 45% or more is released in about 1 hour or less, about 80% or more is released in about 2 hours or less, and about 100% or more is released in about 3 hours or less.

The present inventive methods and formulations also provide pH-independent modified-release formulations comprising drug or pro-drug, or a pharmaceutically acceptable salt thereof, that when measured by a U.S. Pharmacopoeia (USP) Type 1 Apparatus (baskets) or U.S. Pharmacopoeia (USP) Type 2 Apparatus (paddles) at 37° C. and 50 rpm or higher in phosphate buffer at pH 6.8 or higher for the measuring period, release less than or equal to about 30%, less than about 20%, or less than about 10% of the drug or pro-drug, in vitro in less than about 1 hours; release less than or equal to about 60%, less than about 50%, or less than about 40%, in about 4 or more hours; and release greater than or equal to about 70%, greater than about 80%, or greater than about 90% in about 12 or more hours.

More particularly, pH-independent modified-release formulations according to the present invention can exhibit dissolution profiles, when measured by a U.S. Pharmacopoeia (USP) Type 1 Apparatus (baskets) or U.S. Pharmacopoeia (USP) Type 2 Apparatus (paddles) at 37° C. and 50 rpm or higher in phosphate buffer at pH 6.8 or higher for the measuring period, falling within the following windows: 1 hour: less than or equal to about 20%; 2 hours: from about 0 to about 35%; 3 hours: from about 10 to about 60%; 4 hours: from about 20 to about 60%; 6 hours: from about 40 to about 80%; and 12 hours: greater than or equal to about 75%. In other embodiments, the dissolution profiles can fall within the following windows: 1 hour: less than or equal to about 5%; 2 hours: from about 0 to about 25%; 3 hours: from about 15 to about 30%; 4 hours: from about 40 to about 50%; 6 hours: from about 60 to about 75%; and 12 hours: greater than or equal to about 90%. Note that formulations of this invention may fall within one or more of these dissolution windows.

Formulations, which can be pH-dependent modified-release formulations, according to the present invention, when measured by a U.S. Pharmacopoeia (USP) Type 1 Apparatus (baskets) or U.S. Pharmacopoeia (USP) Type 2 Apparatus (paddles) at 37° C. and 50 rpm or higher in 0.01 to 0.1N HCl for two hours, followed by phosphate buffer at pH 6.8 or higher for the remaining measuring period, can exhibit dissolution profiles falling within one or more of these dissolution windows: 1 hour (in acid), about 0 to about 10% released; 2 hours (in acid), about 0 to about 10% released; 1 hour (in buffer), about 10 to about 35% released; 2 hours (in buffer), about 20 to about 65% released; 4 hours (in buffer), about 55 to about 95% released; 6 hours (in buffer), greater than or equal to about 90% released; and 12 hours (in buffer), about 90% or greater released. In other embodiments, the inventive formulations can exhibit dissolution profiles falling within one or more of these dissolution windows: 1 hour (in acid), about 0 to about 5% released; 2 hours (in acid), about 0 to about 5% released; 1 hour (in buffer), about 15 to about 30% released; 2 hours (in buffer), about 25 to about 60% released; 4 hours (in buffer), about 60 to about 90% released; 6 hours (in buffer), greater than or equal to about 90% released; and 12 hours (in buffer), about 95% or greater released. Again, it should be noted that formulations of this invention may fall within one or more of these dissolution windows.

The present invention overcomes the deficiencies and problems in the prior art by providing new and effective formulations and methods for reducing, preventing, and/or managing inflammatory bowel disease, and symptoms thereof. The methods for reducing, preventing, and/or managing inflammatory bowel disease involve administering an effective amount of a drug or pro-drug, or a pharmaceutically acceptable salt thereof, to a subject in need of such reduction, prevention, and/or management. The inflammatory bowel disease can be associated with one or more intestinal conditions. Thus, the present invention can also be used to directly or indirectly reduce, prevent, and/or manage such intestinal conditions by the use of these drugs or pro-drugs. Examples of intestinal conditions that can be treated, prevented, and/or managed according to the present invention include, but are not limited to, inflammatory bowel disease (IBD), ulcerative colitis, granulomatous enteritis, Crohn's disease, infectious diseases of the small and large intestine, pyloric spasm, abdominal cramps, functional gastrointestinal disorders, mild dysenteries, diverticulitis, acute enterocolitis, neurogenic bowel disorders, including the splenic flexure syndrome and neurogenic colon, spastic colitis, cysts, polyps, and carcinoma, and/or symptoms of any of the foregoing. Those of ordinary skill in the art will be familiar with other types of intestinal conditions that produce inflammatory bowel disease, which can benefit from the present invention.

As used herein, the term "pharmaceutically acceptable salt" includes salts that are physiologically tolerated by a subject. Such salts can be prepared from an inorganic and/or organic acid. Examples of suitable inorganic acids include, but are not limited to, hydrochloric, hydrobromic, hydroiodic, nitric, sulfuric, and phosphoric acid. Organic acids can be aliphatic, aromatic, carboxylic, and/or sulfonic acids. Suitable organic acids include, but are not limited to, formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

In accordance with the invention, the drug or pro-drug, or a pharmaceutically acceptable salt thereof, is formulated and/or dosed in a manner that maximizes its therapeutic effects, while minimizing at least one systemic side effect.

The present invention also provides methods and formulations for treating inflammatory bowel disease, comprising administering to said subject an effective amount of the drug or pro-drug, or a pharmaceutically acceptable salt thereof, in combination with at least one additional pharmaceutically active compound. Examples of other pharmaceutically active compounds that can be used in combination with the drug or pro-drug include, but are not limited to, steroids (for example, budesonide and other corticosteroids, and adrenal steroids such as prednisone and hydrocortisone), cytokines such as interleukin-10, antibiotics, immunomodulating agents such as azathioprine, 6-mercaptopurine, methotrexate, cyclosporine, and anti-tumor necrosis factor (TNF) agents such as soluble TNF receptor and antibodies raised to TNF, and also antinflammatory agents such as zinc.

The drug or pro-drug, or a pharmaceutically acceptable salt thereof, can be administered with one or more of such pharmaceutically active compounds. Combinations can be administered such that drug or pro-drug, or a pharmaceutically acceptable salt thereof, and the at least one other pharmaceutically active compound are contained in the same dosage form. Alternatively, the combinations can be administered such that drug or pro-drug and the at least one additional pharmaceutically active compound are contained in separate dosage forms and are administered concomitantly or sequentially.

The drug or pro-drug used in accordance with the present invention can be obtained by any method. Examples of such methods are described in, for example, U.S. Pat. Nos. 4,591,584, 4,559,330, and 6,602,915, each of which is incorporated herein by reference for this purpose. Modifications of the protocols described in these patents, as well as other routes of synthesis, are well known to those of ordinary skill in the art and can be employed in accordance with the present invention.

The pharmaceutically acceptable formulations described herein can be provided in the form of a pharmaceutical formulation for use according to the present invention. Such formulations optionally include one or more pharmaceutically acceptable excipients. Examples of suitable excipients are known to those of skill in the art and are described, for example, in the *Handbook of Pharmaceutical Excipients* (Kibbe (ed.), 3$^{rd}$ Edition (2000), American Pharmaceutical Association, Washington, D.C.), and *Remington: The Science and Practice of Pharmacy* (Gennaro (ed.), 20$^{th}$ edition (2000), Mack Publishing, Inc., Easton, Pa.) (hereinafter referred to as "Remington"), both of which, for their disclosures relating to excipients and dosage forms, are incorporated herein by reference. Suitable excipients include, but are not limited to, starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, plasticizers, gelling agents, thickeners, hardeners, setting agents, suspending agents, surfactants, humectants, carriers, stabilizers, antioxidants, and combinations thereof.

Formulations suitable for oral administration include, but are not limited to, capsules, cachets, pills, tablets, lozenges (using a flavored base, usually sucrose and acacia or tragacanth), powders, granules, solutions, suspensions in an aqueous or non-aqueous liquid, oil-in-water or water-in-oil liquid emulsions, elixirs, syrups, pastilles (using an inert base, such as gelatin and glycerin, or sucrose and acacia), mouth washes, pastes, and the like, each containing a predetermined amount of drug or pro-drug, or a pharmaceutically acceptable salt thereof, to provide a therapeutic amount of the drug in one or more doses.

The drug or pro-dug, or a pharmaceutically acceptable salt thereof, can be mixed with pharmaceutically acceptable excipients in the preparation of dosage forms for oral administration (capsules, tablets, pills, powders, granules and the like). Suitable excipients include, but are not limited to, carriers, such as sodium citrate or dicalcium phosphate; fillers or extenders, such as starches, lactose, sucrose, glucose, mannitol, or silicic acid; binders, such as hydroxymethyl-cellulose, alginates, gelatin, polyvinylpyrrolidone, sucrose or acacia; humectants, such as glycerol; disintegrating agents, such as agar, calcium carbonate, potato or tapioca starch, alginic acid, certain silicates, or sodium carbonate; solution retarding agents, such as paraffin; absorption accelerators, such as quaternary ammonium compounds; wetting agents, such as cetyl alcohol or glycerol monostearate; absorbents, such as kaolin and bentonite clay; lubricants, such as talc, calcium stearate, magnesium stearate, solid polyethylene glycols, and sodium lauryl sulfate; coloring agents; buffering agents; dispersing agents; preservatives; and diluents.

The aforementioned excipients are given as examples only and are not meant to include all possible choices. Solid formulations can also be employed as fillers in soft and hard-filled gelatin capsules using excipients such as lactose or milk sugars, high molecular weight polyethylene glycols, and the like. Any of these dosage forms can optionally be scored or prepared with coatings and shells, such as enteric coatings and coatings for modifying the rate of release, examples of which are well known in the pharmaceutical-formulating art.

Such coatings can comprise sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, wax, or zein. In one embodiment, the coating material comprises hydroxypropyl methylcellulose. The coating material can further comprise anti-adhesives, such as talc; plasticizers (depending on the type of coating material selected), such as castor oil, diacetylated monoglycerides, dibutyl sebacate, diethyl phthalate, glycerin, polyethylene glycol, propylene glycol, triacetin, triethyl citrate; opacifiers, such as titanium dioxide; and/or coloring agents and/or pigments. The coating process can be carried out by any suitable means, for example, by using a perforated pan system such as the GLATTT™, ACCELA-COTA™, and/or HICOATER™ apparatuses.

Tablets can be formed by any suitable process, examples of which are known to those of ordinary skill in the art. For example, the ingredients can be dry-granulated or wet-granulated by mixing in a suitable apparatus before tabletting.

Granules of the ingredients to be tabletted can also be prepared using suitable spray/fluidization or extrusion/spheronization techniques.

The tablets can be formulated with suitable excipients to act as a fast dissolving and/or fast melting tablet in the oral cavity. Also, the tablet can be in the form of a chewable or effervescent dosage form. With effervescent dosage forms, the tablet can be added to a suitable liquid that causes it to disintegrate, dissolve, and/or disperse.

Tablets can be designed to have an appropriate hardness and friability to facilitate manufacture on an industrial scale using equipment to produce tablets at high speed. Also, the tablets can be packed or filled in any kind of container. It should be noted that the hardness of tablets, amongst other properties, can be influenced by the shape of the tablets. Different shapes of tablets can be used according to the present invention. Tablets can be circular, oblate, oblong, or any other shape. The shape of the tablets can also influence the disintegration rate.

Any of the inventive formulations can be encapsulated in soft and hard gelatin capsules, which can also include any of the excipients described above. For example, the encapsulated dosage form can include fillers, such as lactose and microcrystalline; glidants, such as colloidal silicon dioxide and talc; lubricants, such as magnesium stearate; and disintegrating agents, such as starch (e.g., maize starch). Using capsule filling equipment, the ingredients to be encapsulated can be milled together, sieved, mixed, packed together, and then delivered into a capsule. Lubricants can be present in an amount of from about 0.5% (w/w) to about 2.0% (w/w).

The formulations of the invention, which comprise drug or pro-drug, or a pharmaceutically acceptable salt thereof, can also be formulated into a liquid dosage form for oral administration. Suitable formulations can include emulsions, microemulsions, solutions, suspensions, syrups, and elixirs. The drug or pro-drug can be formulated as an ion-exchange resin complex, a microencapsulated particle, a liposome particle, or a polymer coated particle or granule. These formulations optionally include diluents commonly used in the art, such as, for example, water or other solvents, solubilizing agents and emulsifiers. Emulsifiers include, but are not limited to, ethyl alcohol, isopropyl alcohol, ethyl carbonate, ethyl acetate, benzyl alcohol, benzyl benzoate, propylene glycol, 1,3-butylene glycol, oils, glycerol, tetrahydrofurfuryl alcohol, polyethylene glycols, fatty acid esters of sorbitan, and mixtures thereof. In addition, the inventive formulations can include adjuvants such as wetting agents, emulsifying and suspending agents, sweetening, flavoring, coloring, perfuming, and preservative agents. Suitable suspension agents include, but are not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof. The liquid formulations can be delivered as-is, or can be provided in hard or soft capsules, for example.

The amount of suspending agent present will vary according to the particular suspending agent used, and the presence or absence of other ingredients that have an ability to act as a suspending agent or contribute significantly to the viscosity of the formulation. The suspension can also contain ingredients that improve its taste, for example sweeteners; bitter-taste maskers, such as sodium chloride; taste-masking flavors, such as contramarum; flavor enhancers, such as monosodium glutamate; and flavoring agents. Examples of sweeteners include bulk sweeteners, such as sucrose, hydrogenated glucose syrup, the sugar alcohols sorbitol and xylitol; and sweetening agents such as sodium cyclamate, sodium saccharin, aspartame, and ammonium glycyrrhizinate. The liquid formulations can further comprise one or more buffering agents, as needed, to maintain a desired pH.

The liquid formulations of the present invention can also be filled into soft gelatin capsules. The liquid can include a solution, suspension, emulsion, microemulsion, precipitate, or any other desired liquid media carrying the pharmaceutically active compound. The liquid can be designed to improve the solubility of the pharmaceutically active compound upon release, or can be designed to form a drug-containing emulsion or dispersed phase upon release. Examples of such techniques are well known in the art. Soft gelatin capsules can be coated, as desired, with a functional coating. Such functional coatings generally serve the purpose of delaying the release of the drug for a predetermined period. For example, such coatings can allow the dosage form to pass through the stomach without being subjected to stomach acid or digestive juices. Thus, such coatings can dissolve or erode upon reaching a desired point in the gastrointestinal tract, such as the upper intestine.

For rectal administration, the inventive formulations can be provided as a suppository. Suppositories can comprise one or more non-irritating excipients such as, for example, polyethylene glycol, a suppository wax, or a salicylate. Such excipients can be selected on the basis of desirable physical properties. For example, a compound that is solid at room temperature but liquid at body temperature will melt in the rectum and release the active compound. The formulation can alternatively be provided as an enema for rectal delivery.

The amount of the dose administered, as well as the dose frequency, will vary depending on the particular dosage form used and the route of administration. The amount and frequency of administration will also vary according to the age, body weight, and response of the individual subject. Typical dosing regimens can readily be determined by a competent physician without undue experimentation. It is also noted that the clinician or treating physician will know how and when to interrupt, adjust, or terminate therapy in conjunction with individual subject response.

In general, the total daily dosage for reducing, preventing, and/or managing the inflammatory bowel disease and/or the intestinal conditions that cause the same, with any of the formulations according to the present invention, is from about 250 mg to about 8000 mg, or from about 500 mg to about 8000 mg, or from about 1000 mg to about 6000 mg, or from about 2000 mg to about 4000 mg. Pro-drugs should be formulated to deliver an equivalent dose. A single oral dose can be formulated to contain about 100 mg, 250 mg, 500 mg, 750 mg, 1000 mg, 1500 mg, 2000 mg, or 3000 mg, or any amount in between.

The pharmaceutical formulations containing drug and/or pro-drug, or a pharmaceutically acceptable salt thereof, can be administered in single or divided doses, 1, 2, 3, 4, 5, or more times each day. Alternatively, the dose can be delivered one or more times every 2, 3, 4, 5, 6, 7, or more days. In one embodiment, the pharmaceutical formulations are administered once per day.

The invention is further illustrated by reference to the following examples. It will be apparent to those skilled in the art that many modifications, both to the materials and methods, can be practiced without departing from the purpose and scope of the invention.

EXAMPLES

Example 1

Effect of Disodium 4,4'-Azo-Bis Salicylate on Inflammatory Bowel Disease

A subject is diagnosed with mild to moderate ulcerative colitis or Crohn's Disease. The subject receives a daily administration of 2 grams per day of disodium 4,4'-azo-bis salicylate. The subject is treated for 12 weeks. The subject keeps daily diaries and records the number and nature of bowel movements. The effect of the treatments is assessed by grading clinical symptoms of fecal blood, mucus, and urgency. In addition, sigmoidoscopic assessment and biopsies are performed, and efficacy of treatment assessed, based on grading of sigmoidoscopic and degree of histological inflammation in rectal biopsy specimens. Safety is assessed based on spontaneous side effect reporting.

Example 2

Modified Release Matrix Tablet Formulations of 4-Aminosalicylate Sodium Using Methocel Premium

Wet Granulation Method

The 4-aminosalicylate sodium is formulated in a matrix tablet that achieves the following target dissolution profiles.
Target Dissolution Profiles
Matrix Tablet without functional coating.

| Time (Hours) pH 6.8 Buffer | % Released |
|---|---|
| 1 | 20 |
| 2 | 35 |
| 3 | 55 |
| 4 | 60 |
| 6 | 72 |
| 12 | 100 |

Matrix Tablet with functional coating (pH-independent Type A).

| Time (Hours) pH 6.8 Buffer | % Released |
|---|---|
| 1 | 0 |
| 2 | 22 |
| 3 | 30 |
| 4 | 55 |
| 6 | 68 |
| 12 | 95 |

Matrix Tablet with functional coating (pH-independent Type B).

| Time (Hours) pH 6.8 Buffer | % Released |
|---|---|
| 1 | 0 |
| 2 | 0 |
| 3 | 14 |
| 4 | 22 |
| 6 | 41 |
| 12 | 76 |

Matrix Tablet with functional coating (pH-dependent).

| Time (Hours) | % Released |
|---|---|
| Acid | |
| 1 | 0 |
| 2 | 0 |
| pH 6.8 Buffer | |
| 1 | 12 |
| 2 | 27 |
| 4 | 63 |
| 6 | 91 |

Matrix Tablet Formulation
The uncoated Matrix Tablet Formulation and processing details are given below.
Composition

| Ingredient | FUNCTION | Mg/tab | Mg/tab | Mg/tab |
|---|---|---|---|---|
| 4 Aminosalicylate Sodium | Active | 571.76 | 571.76 | 571.76 |
| LACTOSE | Diluent | 78.12 | 28.12 | 12.12 |
| AVICEL PH 101 | Binder diluent | 78.12 | 28.12 | 12.12 |
| METHOCEL *PREMIUM CR | Controlled Release Polymer | 200.00 | 300.00 | 400.00 |
| COLLOIDAL SILICON DIOXIDE | Glidant | 2.00 | 2.00 | 2.00 |
| STEARIC ACID | Lubricant | 20.0 | 20.00 | 20.0 |
| PVP | Binder | 50.0 | 50.0 | 50.0 |
| *ISOPROPYL ALCOHOL | Solvent | N/A | N/A | N/A |
| TOTAL (mg) | N/A | 1000 | 1000 | 1068 |

*Methocel grade can be changed or alternatively can be a suitable controlled-release polymer from the example list.

Process—Wet Granulation Process (Using Composition Above)
1. The ingredients are weighed.
2. The Active, 50% of the Avicel, and 50% of the Lactose are placed in a suitable mixer. (For example, Planetary (Hobart), High Shear (Diosna/Fielder)).
3. The ingredients are mixed for 15 minutes to produce a homogeneous mixture.
4. Mixing is continued, while adding to the mixture the granulating fluid (Sodium/PVP Solution).
5. The ingredients are mixed until a suitable granulation end-point is achieved (add more IPA if needed to produce a suitable granule).
6. The granules are dried (using an oven or fluidization equipment) until an acceptable level of moisture (<about 1%) and IPA (<about 0.5%) is achieved. An infrared moisture balance can be used to ascertain water content, and a gas chromatograph can be used for organic solvents.
7. The dry granulate is passed through suitable comminution equipment (for example, Co-Mill or Fitzpatrick mill) fitted with a suitable sized screen (100-500 micron).
8. The granulate is placed in a blender, and the colloidal Silicon Dioxide and the remainder of the Lactose and Avicel are added.

9. The mixture is blended for 15 minutes.

10. The Stearic Acid is added and mixed for 5 more minutes.

11. The mixture is compressed into oval shaped tablets (target weight 1000 mg) on a suitable tablet machine.

Alternatively, the 4-aminosalicylate sodium can be dissolved in the IPA (or alternative solvent), and the PVP can be mixed in the dry blend (prior to granulation).

Functional Coating of the Matrix Tablet

The above-described matrix tablet formulation can be coated with a functional coat. This may be pH-dependent or pH-independent. Examples of both types of coating are given below.

pH-Independent Coating

Two types of pH-independent polymer systems are described, that can be used for coating the matrix tablets described above. (Note that although they are described as being used in a matrix system, these coatings can be used in non-matrix systems, including the coating of immediate-release systems.)

Composition—Polymer System A

| Ingredient | FUNCTION | (Batch g) |
|---|---|---|
| METHOCEL | Controlled Release Polymer | 750.00 |
| ETHOCEL | Controlled Release Polymer | 250.0 |
| TRIETHYL CITRATE | Plasticizer | 12.00 |
| IPA | Solvent | 2000 |
| TOTAL | | 3012 |

Process

1. The tablets are loaded into a suitable coating machine (e.g., Glatt, Acelacota).

2. The Polymer coating solution is sprayed onto the tablets.

3. When the required amount of polymer coating solution has been applied, the tablets are dried on the coating machine.

Composition—Polymer System B

| Ingredient | FUNCTION | (Batch g) |
|---|---|---|
| EUDRAGIT RS 12.5 | Controlled Release Polymer | 900.00 |
| EUDRAGIT RL 12.5 | Controlled Release Polymer | 300.00 |
| TALC | Antiadherent | 105.00 |
| DIBUTYL SEBECATE | Plasticizer | 15.00 |
| MAGNESIUM STEARATE | Antiadherant | 30.00 |
| ACETONE | Solvent | 825.00 |
| ISOPROPYL ALCOHOL | Solvent | 825 |
| TOTAL | | 3000.00 |

Process

1. The tablets are loaded into a suitable coating machine (e.g., Glatt, Acelacota).

2. The Polymer coating solution is sprayed onto the tablets.

3. Once the required amount of polymer coating solution has been applied, the tablets are dried in the coating machine.

pH-Dependent Coating

| Ingredient | FUNCTION | Qty % (w/w) | Batch 1 mg/tab |
|---|---|---|---|
| EUDRAGIT L 100 | Polymer | 6.39 | 6.00 |
| ACETYL TRIBUTYL CITRATE | Plasticizer | 1.60 | 1.50 |
| WATER* | Solvent | 3.26 | N/A |
| ETHANOL* | Solvent | 88.75 | N/A |
| TOTAL | | 100.00 | |

1. The tablets are loaded into a suitable coating machine (e.g., Glatt, Acelacota).

2. The Polymer coating solution is sprayed onto the tablets.

3. Once the required amount of polymer coating solution has been applied, the tablets are dried in a coating machine.

Example 3

Modified Release Formulations of 4-Aminosalicylate Sodium Using a Membrane-Modified Tablet The 4-aminosalicylate sodium is formulated in a Membrane-Modified Tablet to achieve the following dissolution profiles.

Target Dissolution Profiles

Membrane-Modified Tablet without functional coating.

| Time (Hours) pH 6.8 Buffer | % Released |
|---|---|
| 1 | 45 |
| 2 | 80 |
| 3 | 100 |

Membrane-Modified Tablet with functional coating (pH independent Type A).

| Time (Hours) pH 6.8 Buffer | % Released |
|---|---|
| 1 | 0 |
| 2 | 13 |
| 3 | 24 |
| 4 | 37 |
| 6 | 61 |
| 12 | 90 |

Membrane-Modified Tablet with functional coating (pH-independent Type B).

| Time (Hours) pH 6.8 Buffer | % Released |
|---|---|
| 1 | 0 |
| 2 | 0 |

| Time (Hours) pH 6.8 Buffer | % Released |
|---|---|
| 3 | 21 |
| 4 | 44 |
| 6 | 80 |
| 12 | 100 |

Membrane-Modified Tablet with functional coating (pH-dependent).

| Time (Hours) | % Released |
|---|---|
| Acid | |
| 1 | 0 |
| 2 | 0 |
| pH 6.8 Buffer | |
| 1 | 30 |
| 2 | 58 |
| 4 | 91 |
| 6 | 100 |

In each of these examples, the product comprises an instant-release tablet core coated with the diffusion-controlled Membrane. The formulations and manufacturing process for these are given below.

Instant-Release Core Formulation
Composition

| Ingredient | FUNCTION | Qty mg/tab | Qty Batch g |
|---|---|---|---|
| 4AMINOSALICYLATE SODIUM | Active | 571.76 | 571.76 |
| LACTOSE ANHYDROUS | Diluent | 86.12 | 86.12 |
| MICROCRYSTALLINE CELLULOSE | Diluent | 86.12 | 86.12 |
| PVP K30 | Binder | 40.0 | 40.0 |
| STEARIC ACID | Lubricant | 16.0 | 16.0 |
| TOTAL | | 800.00 | 800.00 |

Process
Option 1:
1. The ingredients are weighed using a suitable balance.
2. The 4-aminosalicylate Sodium, Avicel, and Lactose are placed into a suitable granulator (e.g., high shear mixer-Diosna/Fielder).
3. Mix until a homogeneous blend is produced.
4. The PVP is dissolved in water and slowly add to the powder blend.
5. Once all the binder solution has been added to the powder blend, mixing is continued until a suitable granulation as been achieved.
6. The granules are dried in a fluidized drying machine or tray drier until a suitable dryness is achieved. An infrared moisture balance can be used to ascertain water content, and a gas chromatograph can be used for organic solvents.
7. The dry granulate is then milled.
8. The dry granulate is placed in a suitable blender (V or Y type blender), and the lubricant is added and mixed for 5 minutes.
9. The mixture is compressed into tablets (800 mg weight) on a suitable tablet machine.

Option 2:
Alternatively, 50% of the Lactose and Avicel can be used in Step 2 of the process. Once the dry granulate is produced, the remaining 50% of the Lactose and Avicel can be added to the mixer, mixed for 10 minutes. Then proceed to step 9 of the process described for Option 1.

Option 3:
In another alternative, the Active, Lactose, Avicel, and the PVP can be dry granulated, i.e., compressed into a dry granulator using a roller compactor. The roller compacted material can then be passed through a suitable screen to produce granules. These granules can then be mixed with the lubricant (i.e., Stearic acid) as in step 9 of the process.

Diffusion-Controlled Membrane Coating Formulation
Composition

| Ingredient | Option A mg/tab | Option B mg/tab | Option C mg/tab |
|---|---|---|---|
| POLYMER | 11.00 | 9.20 | 11.00 |
| SUCROSE | 29.00 | 17.00 | 21.00 |
| ACETYL TRIBUTYL CITRATE | 2.00 | 1.60 | 1.90 |
| CASTOR OIL POLYMERISED | 1.00 | 1.2 | 1.4 |
| SODIUM HYDROGEN CARBONATE | 1.00 | 1.00 | 1.00 |
| ACETONE* | N/A | N/A | N/A |
| TOTAL | | | |

Polymer = terpolymer of polyvinyl chloride, polyvinyl acetate and polyvinyl alcohol (terpolymer PVC/PVAc/PVOH)
*Solvent is removed during processing.

Process
1. The tablets are loaded into a suitable coating machine (e.g., Glatt, Acelacota).
2. The Polymer coating solution is sprayed onto the tablets.
3. Once the required amount of polymer coating solution has been applied, the tablets are dried on the coating machine.

Functional Coating of the Membrane-Modified Tablet

The above selectively permeable membrane tablet formulation (i.e., the diffusion-controlled membrane-coated tablet) can be additionally coated with a functional coat. This may be pH-dependent or pH-independent. Examples of both types of coating are given below.

pH-Dependant Coating
Composition

| Ingredient | FUNCTION | Qty % (w/w) |
|---|---|---|
| EUDRAGIT L 100 | Polymer | 6.39 |
| ACETYL TRIBUTYL CITRATE | Plasticizer | 1.60 |
| WATER* | Solvent | 3.26 |
| ETHANOL* | Solvent | 88.75 |
| TOTAL | | 100.00 |

Process
1. The tablets are loaded into a suitable coating machine (e.g., Glatt, Acelacota).
2. The Polymer coating solution is sprayed onto the tablets.
3. Once the required amount of polymer coating solution has been applied, the tablets are dried on the coating machine.

pH-Independent Coating System
Two types of pH-independent polymer systems are described for use in coating the tablets described above.

Composition—Polymer System A

| Ingredient | FUNCTION | (Batch g) |
|---|---|---|
| ETHOCEL | Controlled Release Polymer | 760.00 |
| METHOCEL | Controlled Release Polymer | 330.0 |
| ACETYL TRIBUTYL CITRATE | Plasticizer | 220.00 |
| ETHANOL | Solvent | 2680 |
| WATER | Solvent | 451 |
| TOTAL | | 4441 |

1. The tablets are loaded into a suitable coating machine (e.g., Glatt, Acelacota).
2. The Polymer coating solution is sprayed onto the tablets.
3. Once the required amount of polymer coating solution has been applied, the tablets are dried on the coating machine.

Composition—Polymer System B

| Ingredient | FUNCTION | (Batch g) |
|---|---|---|
| EUDRAGIT RS 12.5 | Controlled Release Polymer | 900.00 |
| EUDRAGIT RL 12.5 | Controlled Release Polymer | 300.00 |
| TALC | Ant adherent | 105.00 |
| DIBUTYL SEBECATE | Plasticizer | 15.00 |
| MAGNESIUM STEARATE | Antiadherant | 30.00 |
| ACETONE | Solvent | 825.00 |
| ISOPROPYL ALCOHOL | Solvent | 825 |
| TOTAL | | 3000.0 |

1. The tablets are loaded into a suitable coating machine (e.g., Glatt, Acelacota).
2. The Polymer coating solution is sprayed onto the tablets.
3. Once the required amount of polymer coating solution has been applied, the tablets are dried on the coating machine.

Example 4

Modified Release Disodium 4,4'-Azo-Bis-Salicylate Membrane-Modified Tablet Formulations The disodium 4,4'-azo-bis-4-aminosalicylate sodium is formulated as a Modified-Release tablet using a diffusion-controlled membrane, with the following target dissolution profiles.

Target Dissolution Profiles
Membrane-Modified Tablet without functional coating.

| Time (Hours) pH 6.8 Buffer | % Released |
|---|---|
| 1 | 45 |
| 2 | 80 |
| 3 | 100 |

Membrane-Modified Tablet with functional coating (pH independent Type A).

| Time (Hours) pH 6.8 Buffer | % Released |
|---|---|
| 1 | 0 |
| 2 | 13 |
| 3 | 24 |
| 4 | 37 |
| 6 | 61 |
| 12 | 90 |

Membrane-Modified Tablet with functional coating (pH-independent Type B).

| Time (Hours) pH 6.8 Buffer | % Released |
|---|---|
| 1 | 0 |
| 2 | 0 |
| 3 | 21 |
| 4 | 44 |
| 6 | 80 |
| 12 | 100 |

Membrane-Modified Tablet with functional coating (pH-dependent).

| Time (Hours) | % Released |
|---|---|
| Acid | |
| 1 | 0 |
| 2 | 0 |
| pH 6.8 Buffer | |
| 1 | 30 |
| 2 | 58 |
| 4 | 91 |
| 6 | 100 |

Instant Release Core Formulation
Composition

| Ingredient | FUNCTION | Qty mg/tab | Qty Batch g |
|---|---|---|---|
| Azo-bis-4 AminoSalicylate Sodium | Active | 571.76 | 571.76 |
| LACTOSE ANHYDROUS | Diluent | 86.12 | 86.12 |
| MICROCRYSTALLINE CELLULOSE | Diluent | 86.12 | 86.12 |
| PVP K30 | Binder | 40.0 | 40.0 |
| STEARIC ACID | Lubricant | 16.0 | 16.0 |
| TOTAL | | 800.00 | 800.00 |

Process
Option 1:
1. The ingredients are weighed using a suitable balance.
2. The 4-aminosalicylate Sodium, Avicel, and Lactose are placed into a suitable granulator (e.g., high shear mixer-Diosna/Fielder).
3. Mix until a homogeneous blend is produced).
4. The PVP is dissolved in water and slowly add to the powder blend.
5. Once all the binder solution has been added to the powder blend, mixing is continued until a suitable granulation as been achieved.
6. The granules are dried in a fluidized drying machine or tray drier until a suitable dryness is achieved.

7. The dry granulate is then milled.

8. The dry granulate is placed in a suitable blender (V or Y type blender), and the lubricant is added and mixed for 5 minutes.

9. The mixture is compressed into tablets (800 mg weight) on a suitable tablet machine.

Option 2:

Alternatively, 50% of the Lactose and Avicel can be used in Step 2 of the process. Once the dry granulate is produced, the remaining 50% of the Lactose and Avicel can be added to the mixer, mixed for 10 minutes. Then proceed to step 9 of the process.

Option 3:

In another alternative, the Active, Lactose, Avicel, and the PVP can be dry granulated, i.e., compressed into a dry granulator using a roller compactor. The roller compacted material can then be passed through a suitable screen to produce granules. These granules can then be mixed with the lubricant (i.e., Stearic acid) as in step 9 of the process.

Diffusion-Controlled Membrane Coating Formulation

Composition

| Ingredient | Option A mg/tab) | Option B mg/tab | Option C mg/tab |
|---|---|---|---|
| POLYMER | 11.00 | 9.20 | 11.00 |
| SUCROSE | 29.00 | 17.00 | 21.00 |
| ACETYL TRIBUTYL CITRATE | 2.00 | 1.60 | 1.90 |
| CASTOR OIL POLYMERISED | 1.00 | 1.2 | 1.4 |
| SODIUM HYDROGEN CARBONATE | 1.00 | 1.00 | 1.00 |
| ACETONE* | N/A | N/A | N/A |
| TOTAL | 44.00 | 30.00 | 36.30 |

Polymer = terpolymer of polyvinyl chloride, polyvinyl acetate and polyvinyl alcohol (terpolymer PVC/PVAc/PVOH)
*Solvent is removed during processing.

Process

1. The tablets are loaded into a suitable coating machine (e.g., Glatt, Acelacota).

2. The Polymer coating solution is sprayed onto the tablets.

3. Once the desired amount of polymer coating solution has been applied, the tablets are dried on the coating machine.

Functional Coating of the Membrane-Modified Tablet

The above selectively permeable membrane tablet formulation (i.e., the membrane-modified tablet) can be additionally coated with a functional coat. This may be pH-dependent or pH-independent. Examples of both types of coating are given below.

pH-Dependent Coating

Composition

| Ingredient | FUNCTION | Qty % (w/w) |
|---|---|---|
| EUDRAGIT L 100 | Polymer | 6.39 |
| ACETYL TRIBUTYL CITRATE | Plasticizer | 1.60 |
| WATER* | Solvent | 3.26 |
| ETHANOL* | Solvent | 88.75 |
| TOTAL | | 100.00 |

Process

1. The tablets are loaded into a suitable coating machine (e.g., Glatt, Acelacota).

2. The Polymer coating solution is sprayed onto the tablets.

3. Once the required amount of polymer coating solution has been applied, the tablets are dried on the coating machine.

pH-Independent Coating System

Two types of pH-independent polymer systems are described for use in coating the tablets described above.

Composition—Polymer System A

| Ingredient | FUNCTION | (Batch g) |
|---|---|---|
| ETHOCEL | Controlled Release Polymer | 760.00 |
| METHOCEL | Controlled Release Polymer | 330.0 |
| ACETYL TRIBUTYL CITRATE | Plasticizer | 220.00 |
| ETHANOL | Solvent | 2680 |
| WATER | Solvent | 451 |
| TOTAL | | 4441 |

Process

1. The tablets are loaded into a suitable coating machine (e.g., Glatt, Acelacota).

2. The Polymer coating solution is sprayed onto the tablets.

3. Once the required amount of polymer coating solution has been applied, the tablets are dried on the coating machine.

Composition—Polymer System B

| Ingredient | FUNCTION | (Batch g) |
|---|---|---|
| EUDRAGIT RS 12.5 | Controlled Release Polymer | 900.00 |
| EUDRAGIT RL 12.5 | Controlled Release Polymer | 300.00 |
| TALC | Ant adherent | 105.00 |
| DIBUTYL SEBECATE | Plasticizer | 15.00 |
| MAGNESIUM STEARATE | Antiadherant | 30.00 |
| ACETONE | Solvent | 825.00 |
| ISOPROPYL ALCOHOL | Solvent | 825 |
| TOTAL | | 3000.0 |

Process

1. The tablets are loaded into a suitable coating machine (e.g., Glatt, Acelacota).

2. The Polymer coating solution is sprayed onto the tablets.

3. Once the required amount of polymer coating solution has been applied, the tablets are dried on the coating machine.

Example 5

Modified Release Formulations of Disodium 4,4'-Azo-Bis-Salicylate Using Methocel Premium at Various Levels (Wet Granulation Method)

The 4,4'-azo-bis-salicylate is formulated in a matrix tablet to achieve the following target dissolution profiles.

Target Dissolution Profiles

Matrix Tablet without functional coating.

| Time (Hours) pH 6.8 Buffer | % Released |
|---|---|
| 1 | 20 |
| 2 | 35 |
| 3 | 55 |
| 4 | 60 |
| 6 | 72 |
| 12 | 100 |

Matrix Tablet with functional coating (pH-independent Type A).

| Time (Hours) pH 6.8 Buffer | % Released |
|---|---|
| 1 | 0 |
| 2 | 22 |
| 3 | 30 |
| 4 | 55 |
| 6 | 68 |
| 12 | 95 |

Matrix Tablet with functional coating (pH-independent Type B).

| Time (Hours) pH 6.8 Buffer | % Released |
|---|---|
| 1 | 0 |
| 2 | 0 |
| 3 | 14 |
| 4 | 22 |
| 6 | 41 |
| 12 | 76 |

Matrix Tablet with functional coating (pH-dependent).

| Time (Hours) | % Released |
|---|---|
| Acid | |
| 1 | 0 |
| 2 | 0 |
| pH 6.8 Buffer | |
| 1 | 12 |
| 2 | 27 |
| 4 | 63 |
| 6 | 91 |

Matrix Tablet Formulation

The uncoated Matrix Tablet Formulation and processing details are given below.

Composition

| Ingredient | FUNCTION | Mg/tab | Mg/tab | Mg/tab |
|---|---|---|---|---|
| Azo-bis-4-aminosalicylate Sodium | Active | 571.76 | 571.76 | 571.76 |
| LACTOSE | Diluent | 78.12 | 28.12 | 12.12 |
| AVICEL PH101 | Binder diluent | 78.12 | 28.12 | 12.12 |
| METHOCEL *PREMIUM CR | Controlled Release Polymer | 200.00 | 300.00 | 400.00 |
| COLLOIDAL SILICON DIOXIDE | Glidant | 2.00 | 2.00 | 2.00 |
| STEARIC ACID | Lubricant | 20.0 | 20.00 | 20.0 |
| PVP | Binder | 50.0 | 50.0 | 50.0 |
| *ISOPROPYL ALCOHOL | Solvent | N/A | N/A | N/A |
| TOTAL (mg) | N/A | 1000 | 1000 | 1068 |

Methocel grade can be changed or alternatively can be a suitable controlled-release polymer from the example list.

Process—Wet Granulation Process (Using Formulation Above)

1. The ingredients are weighed.

2. The Active, 50% of the Avicel, and 50% of the Lactose are placed in a suitable mixer. (For example, Planetary (Hobart), High Shear (Diosna/Fielder)).

3. The ingredients are mixed for 15 minutes to produce a homogeneous mixture.

4. Mixing is continued, while adding to the mixture the granulating fluid (Sodium/PVP Solution).

5. The ingredients are mixed until a suitable granulation end-point is achieved (add more IPA if needed to produce a suitable granule).

6. The granules are dried (using an oven or fluidization equipment) until an acceptable level of moisture (<about 1%) and IPA (<about 0.5%) is achieved.

7. The dry granulate is passed through suitable comminution equipment (for example, Co-Mill or Fitzpatrick mill) fitted with a suitable sized screen (100-500 micron).

8. The granulate is placed in a blender, and colloidal Silicon Dioxide and the remainder of the Lactose and Avicel are added.

9. The mixture is blended for 15 minutes.

10. The Stearic Acid is added and mixed for 5 more minutes.

11. The mixture is compressed into tablets (target weight 1000 mg) on a suitable tablet machine.

Alternatively, the disodium 4,4'-azo-bis-salicylate can be dissolved in the IPA (or alternative solvent), and the PVP can be mixed in the dry blend (prior to granulation).

Functional Coating of the Matrix Tablet

The above-described matrix tablet formulation can be coated with a functional coat. This may be pH-dependent or pH-independent. Examples of both types of coating are given below.

pH-Independent Coating

Two types of pH-independent polymer systems are described, for use in coating the matrix tablets described above.

Composition—Polymer System A

| Ingredient | FUNCTION | (Batch g) |
|---|---|---|
| ETHOCEL | Controlled Release Polymer | 760.00 |
| METHOCEL | Controlled Release Polymer | 330.0 |
| ACETYL TRIBUTYL CITRATE | Plasticizer | 220.00 |
| ETHANOL | Solvent | 2680 |
| WATER | Solvent | 451 |
| TOTAL | | 4441 |

Process
1. The tablets are loaded into a suitable coating machine (e.g., Glatt, Acelacota).
2. The Polymer coating solution is sprayed onto the tablets.
3. When the required amount of polymer coating solution has been applied, the tablets are dried on the coating machine.

Composition—Polymer System B

| Ingredient | FUNCTION | (Batch g) |
|---|---|---|
| EUDRAGIT RS 12.5 | Controlled Release Polymer | 900.00 |
| EUDRAGIT RL 12.5 | Controlled Release Polymer | 300.00 |
| TALC | Antiadherent | 105.00 |
| DIBUTYL SEBECATE | Plasticizer | 15.00 |
| MAGNESIUM STEARATE | Antiadherant | 30.00 |
| ACETONE | Solvent | 825.00 |
| ISOPROPYL ALCOHOL | Solvent | 825 |
| TOTAL | | 3000.00 |

Process
1. The tablets are loaded into a suitable coating machine (e.g., Glatt, Acelacota).
2. The Polymer coating solution is sprayed onto the tablets.
3. Once the required amount of polymer coating solution has been applied, the tablets are dried in the coating machine.

Composition—pH-Dependent Coating

| Ingredient | FUNCTION | Qty % (w/w) | Batch 1 mg/tab |
|---|---|---|---|
| EUDRAGIT L 100 | Polymer | 6.39 | 6.00 |
| ACETYL TRIBUTYL CITRATE | Plasticizer | 1.60 | 1.50 |
| WATER* | Solvent | 3.26 | N/A |
| ETHANOL* | Solvent | 88.75 | N/A |
| TOTAL | | 100.00 | |

Process
1. The tablets are loaded into a suitable coating machine (e.g., Glatt, Acelacota).
2. The Polymer coating solution is sprayed onto the tablets.
3. Once the required amount of polymer coating solution has been applied, the tablets are dried in a coating machine.

Example 6

Disodium 4,4'-Azo-Bis-Salicylate Formulations

Disodium 4,4'-azo-bis-salicylate is also incorporated into the following formulations Instant Release Tablet Formulations:
1. Instant-release tablet formulation without functional coat.
2. Instant-release tablet formulation with functional coat—pH-dependent.
3. Instant-release tablet formulation with functional coat—pH-independent.

Multiparticulate Formulations
1. Instant-release multiparticulate formulation (without functional coat).
2. Delayed-release multiparticulate formulation with functional coat—pH-dependent.
3. Delayed-release multiparticulate formulation with functional coat—pH-independent.
4. Controlled-release multiparticulate formulation.
5. Delayed release/modified release multiparticulate formulation.

Instant Release Tablet Formulation without Functional Coat:
An instant release tablet formulation and manufacturing process is described below.

Composition (Immediate Release Tablet Formulation)

| Ingredient | FUNCTION | Qty % (w/w) |
|---|---|---|
| 4ASA-4ASA AZO SODIUM SALT | Active | 571.76 |
| LACTOSE | Diluent | 128.12 |
| AVICEL PH101 | Dry Binder/diluent | 128.12 |
| SODIIUM STARCH GLYCOLATE (EXPLOTAB) | Disintegrant | 100.00 |
| COLLOIDAL SILICON DIOXIDE | Glidant | 2.0 |
| STEARIC ACID | Lubricant | 20.00 |
| PVP | Binder | 50.00 |
| *ISOPROPYL ALCOHOL | Solvent | N/A |
| TOTAL | | 1000 |

*Removed during processing.

Wet Granulation Process (Using Formulation Above)
1. The ingredients are weighed.
2. The PVP is dissolved in the IPA.
3. The 4-ASA-4ASA azo sodium salt, 50% of the Avicel, and 50% of the Lactose are combined in a suitable mixer. (Planetary (Hobart), High Shear (Diosna/Fielder)).
4. The ingredients are mixed for 15 minutes to produce a homogeneous mixture.
5. Mixing is continued and the granulating fluid (PVP Solution) is added to the mixture.
6. Mixing is continued until a suitable granulation end point is achieved (add more IPA if needed to produce a suitable granule).

7. The granules are dried (oven or fluidization equipment) until acceptable level of moisture (<about 1%) and IPA (<about 0.5%) is achieved.

8. The dry granulate is passed through suitable comminution equipment (Co-Mill, Fitzpatrick mill) fitted with a suitable sized screen (100-500 micron).

9. The granulate is placed in a blender and colloidal silicon dioxide, Sodium Starch Glycolate, and the remainder of the Lactose and Avicel are added.

10. The combination is mixed for 15 minutes.

11. The Stearic Acid is added and the combination is mixed for 5 more minutes.

12. The mixture is compressed into tablets (target weight 500/1000 mg) on a suitable tablet machine.

Modified-Release Multiparticulate Formulation of Disodium 4,4'-Azo-Bis-Salicylate A. Instant-Release Drug-Loaded Multiparticulates Without Functional Coat A multiparticulate dosage form for the instant release formulation and manufacturing process is given below.

Composition (Immediate Release Multiparticulates)

| Ingredient | FUNCTION | Qty (mg/g) |
|---|---|---|
| 4ASA-4ASA AZO SODIUM SALT | Active | 571.76 |
| NON PAREIL SEEDS | Inert carrier | 228.24 |
| PVP | Binder | 50.00 |
| TALC | Antiadherent | 125.0 |
| COLLOIDAL SILICON DIOXIDE | Glidant | 25.00 |
| SUITABLE SOLVENT | Solvent | N/A |
| TOTAL | | 1000 |

1. The disodium 4,4'-azo-bis-salicylate, binder, glidant, and anti-adherent are dissolved/suspended in a suitable solvent.

2. The solution/suspension is then sprayed onto the sugar spheres using an appropriate fluidized coating machine (e.g., Glatt).

3. Once all the solution suspension has been applied on to the nonpareil seeds, the drug-loaded instant-release multiparticulates are dried in the fluidized coating machine.

The Instant release multiparticulates and tablets described above are coated with a combination of different modified-release polymers to produce a number of different types of modified-release multiparticulates, which are described below.

B. Modified-Release tablets and/or multiparticulate formulation of disodium 4,4'-azo-bis-salicylate using Polymer system A.

Composition—Polymer System A

| Ingredient | FUNCTION | (Batch g) |
|---|---|---|
| EUDRAGIT RS 30D | Controlled Release Polymer | 200.00 |
| TALC | Antiadherent | 60.00 |
| TRIETHYL CITRATE | Plasticizer | 12.00 |
| SIMETHICONE EMULSION | Dispersant | 1.00 |

-continued

| Ingredient | FUNCTION | (Batch g) |
|---|---|---|
| WATER | Solvent | 392.00 |
| TOTAL | | 665.00 |

Process

1. The drug-loaded instant-release multiparticulates or tablets are loaded into a suitable fluidized coating machine (e.g., Glatt, Acelacota).

2. The polymer coating solution is sprayed onto the drug-loaded instant-release multiparticulates.

3. Once the required amount of polymer coating solution has been applied, the product is dried in the fluidized coating machine.

4. For multiparticulate products, load the coated multiparticulates in a hard gelatin capsule using an automated encapsulation machine, sufficient to obtain a 250-mg dose of disodium 4,4'-azo-bis-salicylate per capsule.

An instant-release tablet can be coated with this system, resulting in an instant release tablet formulation with functional coat—pH independent, resulting in a delayed release tablet. Also, an instant-release multiparticulate can be coated with this system, resulting in a delayed release multiparticulate formulation with functional coat—pH-independent.

Modified Release Tablet and/or Multiparticulate Formulation of Disodium 4,4'-Azo-Bis-Salicylate Salt Using Polymer System B Composition—Polymer System B

| Ingredient | FUNCTION | (Batch g) |
|---|---|---|
| EUDRAGIT RS 12.5 | Controlled Release Polymer | 900.00 |
| EUDRAGIT RL 12.5 | Controlled Release Polymer | 300.00 |
| TALC | Antiadherent | 105.00 |
| DIBUTYL SEBECATE | Plasticizer | 15.00 |
| STEARIC ACID | Antiadherant | 30.00 |
| ACETONE | Solvent | 825.00 |
| ISOPROPYL ALCOHOL | Solvent | 825 |
| TOTAL | | 3000.00 |

Manufacturing Process—Modified-Release Multiparticulate and/or Tablet Disodium 4,4'-Azo-Bis-Salicylate Formulation Process 1. The drug-loaded instant-release multiparticulates and/or tablets are loaded into a suitable fluidized coating machine (e.g., Glatt).

2. The Polymer coating solution is sprayed onto the drug-loaded instant-release multiparticulates and/or tablets.

3. Once the required amount of polymer coating solution has been applied, the product is dried in the fluidized coating machine.

4. If multiparticulate, the product is encapsulated in a hard gelatin capsule using an automated encapsulation machine, sufficient to obtain a 250-mg dose of disodium 4,4'-azo-bis-salicylate per capsule.

When prepared in this manner, this represents a controlled-release multiparticulate formulation.

Modified Release Tablet and/or Multiparticulate Formulation of Disodium 4,4'-Azo-Bis-Salicylate Using Polymer Solution C Composition—Polymer C Formulation (pH-Dependent)

| Ingredient | FUNCTION | Qty % (w/w) | Batch 1 mg/tab |
|---|---|---|---|
| EUDRAGIT L 100 | Polymer | 6.39 | 6.00 |
| ACETYL TRIBUTYL CITRATE | Plasticizer | 1.60 | 1.50 |
| WATER* | Solvent | 3.26 | N/A |
| ETHANOL* | Solvent | 88.75 | N/A |
| TOTAL | | 100.00 | |

Process

1. The instant-release tablets or multiparticulates are loaded into a suitable coating machine (e.g., Glatt or Acelacota).
2. The Polymer coating solution is sprayed onto the tablets or multiparticulates.
3. Once the required amount of polymer coating solution has been applied, the product is dried in the coating machine.

When prepared in this manner, this represents a delayed-release multiparticulate formulation with functional coat—pH dependent, or a delayed release tablet formulation with functional coat—pH dependent.

Delayed Release/Modified Release Multiparticulate Formulation

The final formulation option is a delayed-release/modified-release tablet and/or multiparticulate formulation. This is produced by coating the instant-release multiparticulates and/or tablets with the Polymer A formulation, followed by coating with either the pH-independent Polymer B formulation or the pH-dependent Polymer C formulation.

Example 7

Biostudy

An open-label, single-dose, four-treatment, four period, balanced, randomized, crossover study is designed to compare and assess the relative bioavailability of three modified-release formulations with an immediate-release reference form. Modified-release formulations are prepared as follows: a) membrane-modified formulation of 4-ASA with Type A functional coating (see Example 3), b) membrane-modified formulation of 4-ASA with Type B functional coating (see Example 3), and c) 5,5-azo-bis-salicylic acid formulated in a membrane-modified formulation (see Example 3, Type A coating).

Sixteen healthy volunteers are dosed on each of four occasions with at least a seven-day washout period between each dose. The volunteers are fasting from food and beverages other than water for at least 4 hours before dosing in each treatment period. Water is proscribed for one hour before and one hour after dosing except for the 150 mL of water at the time of dosing. Venous blood samples are obtained at regular time intervals immediately prior to and following each dosing for a period of up to 48 hours. In addition, urine is collected over the 48-hour post-dosing period. Concentrations of 4-ASA and n-acetylated 4-ASA (N-Ac-4-ASA) in plasma and urine are measured by HPLC using an isocratic system and UV detection at 300 nm. Individual plasma concentration curves are constructed and individual, mean, and relative pharmacokinetic parameters are estimated including Tmax, Cmax and AUC. Total urinary recovery of 4-ASA and the n-acetylated 4-ASA metabolite are estimated.

Example 8

Treatment of Ulcerative Colitis and Crohns Disease with Modified-Release 4-ASA

Modified-release formulations according to Example 3 are prepared. A subject is diagnosed with mild to moderate ulcerative colitis or Crohn's Disease. The subject receives a daily administration of either 4 grams per day 4-ASA, or a pharmaceutically acceptable salt thereof, in a modified-release form. Alternatively, the subject can be given 2 grams per day of 4,4'-azo-bis salicylic acid. Subjects are treated for 12 weeks. Subjects keep daily diaries and record the number and nature of bowel movements. The effect of the treatments is assessed by grading clinical symptoms of fecal blood, mucus, and urgency. In addition, sigmoidoscopic assessment and biopsies are performed, and efficacy of treatment assessed, based on grading of sigmoidoscopic and degree of histological inflammation in rectal biopsy specimens. Safety is assessed based on spontaneous side effect reporting.

The formulations of this example demonstrate efficacy in both ulcerative colitis and Crohn's Disease in terms of both treating the condition and maintaining remission from disease symptoms.

What is claimed is:

1. A pharmaceutical composition comprising: a salicylate and/or salicylic acid chosen from 5-amino salicylic acid, pharmaceutically acceptable salts and esters thereof, and prodrugs thereof; at least one pharmaceutically acceptable excipient; and a polymer system chosen from (a) at least one of methyl cellulose and hydroxypropylmethylcellulose in combination with ethyl cellulose, and (b) at least two ammonio methacrylate co-polymers; wherein the composition is formulated as a modified-release pharmaceutical composition with a modified-release matrix core, wherein the composition exhibits a drug-release profile that is independent of surrounding pH and wherein the composition exhibits the following dissolution profile, when tested in a U.S.P. Type II apparatus (paddles) at 37° C. and 50 rpm, in pH 6.8 buffer for the test:

1 hour: less than or equal to about 10% drug released;
2 hours: from about 0 to about 35% drug released;
3 hours: from about 10 to about 60% drug released;
4 hours: from about 20 to about 60% drug released;
6 hours: from about 40 to about 80% drug released; and
12 hours: from about 75 to about 100% drug released.

2. The pharmaceutical composition according to claim 1, wherein the composition exhibits the following dissolution profile, when tested in a U.S.P. Type II apparatus (paddles) at 37° C. and 50 rpm, in pH 6.8 buffer for the test:

1 hour: less than or equal to about 5% drug released;
2 hours: from about 0 to about 25% drug released;
3 hours: from about 15 to about 30% drug released;
4 hours: from about 40 to about 50% drug released;
6 hours: from about 60 to about 75% drug released; and
12 hours: from about 90 to about 100% drug released.

3. The composition according to claim 1, wherein the salicylate and/or salicylic acid is chosen from 5-amino salicylic acid and pharmaceutically acceptable salts of 5-amino salicylic acid.

4. The composition according to claim 1, wherein the salicylate and/or salicylic acid is chosen from 5,5"-azo-bis salicylic acid and pharmaceutically acceptable salts thereof.

5. The composition according to claim 1, wherein the polymer system comprises hydroxypropylmethylcellulose and ethylcellulose.

6. The composition according to claim 5, wherein the at least one pharmaceutically acceptable excipient comprises hydroxypropylmethylcellulose.

7. The composition according to claim 1, wherein the polymer system comprises at least two ammonio methacrylate co-polymers.

8. The composition according to claim 1, wherein the polymer system comprises a functional coating and a sealant.

9. The composition according to claim 8, wherein the functional coating comprises ethylcellulose and the sealant comprises hydroxypropylmethylcellulose.

* * * * *